United States Patent
Burgess et al.

(10) Patent No.: US 12,377,073 B2
(45) Date of Patent: Aug. 5, 2025

(54) TREATMENTS FOR CHARCOT-MARIE-TOOTH DISEASE

(71) Applicant: The Jackson Laboratory, Bar Harbor, ME (US)

(72) Inventors: Robert W. Burgess, Bar Harbor, ME (US); Emily Spaulding, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 1023 days.

(21) Appl. No.: 17/288,178

(22) PCT Filed: Oct. 25, 2019

(86) PCT No.: PCT/US2019/058045
§ 371 (c)(1),
(2) Date: Apr. 23, 2021

(87) PCT Pub. No.: WO2020/086954
PCT Pub. Date: Apr. 30, 2020

(65) Prior Publication Data
US 2021/0393591 A1 Dec. 23, 2021
US 2022/0387387 A2 Dec. 8, 2022

Related U.S. Application Data

(60) Provisional application No. 62/751,388, filed on Oct. 26, 2018.

(51) Int. Cl.
| | |
|---|---|
| *A61K 31/4162* | (2006.01) |
| *A61K 31/404* | (2006.01) |
| *A61K 45/06* | (2006.01) |
| *A61P 21/00* | (2006.01) |
| *A61P 25/00* | (2006.01) |
| *C12N 15/113* | (2010.01) |
| *C12Q 1/68* | (2018.01) |

(52) U.S. Cl.
CPC ........ *A61K 31/4162* (2013.01); *A61K 31/404* (2013.01); *A61K 45/06* (2013.01); *A61P 21/00* (2018.01); *A61P 25/00* (2018.01); *C12N 15/113* (2013.01)

(58) Field of Classification Search
None
See application file for complete search history.

(56) References Cited

U.S. PATENT DOCUMENTS

2011/0286927 A1  11/2011  Ratan
2015/0164891 A1  6/2015  Hornstein et al.

OTHER PUBLICATIONS

Nakamura. PNAS, 2018, vol. 115, No. 33, E7776-E7785, published Jul. 10, 2018 (Year: 2018).*
PCT/US2019/058045, Jan. 27, 2020, International Search Report and Written Opinion.
PCT/US2019/058045, May 6, 2021, International Preliminary Report on Patentability.
International Search Report and Written Opinion, mailed Jan. 27, 2020 for Application No. PCT/US2019/058045.
International Preliminary Report on Patentability, mailed May 6, 2021 for Application No. PCT/US2019/058045.
Bais et al., Metabolite profile of a mouse model of Charcot-Marie-Tooth type 2D neuropathy: implications for disease mechanisms and interventions. Biol Open. Jul. 15, 2016;5(7):908-20. doi: 10.1242/bio.019273.
Ishimura et al., Activation of GCN2 kinase by ribosome stalling links translation elongation with translation initiation. Elife. Apr. 16, 2016;5:e14295. doi: 10.7554/eLife.14295.
Joe et al., FGF21 induced by carbon monoxide mediates metabolic homeostasis via the PERK/ATF4 pathway. Faseb J. May 2018;32(5):2630-2643. doi: 10.1096/fj.201700709RR. Epub Jan. 2, 2018.
Ma et al., Suppression of eIF2α kinases alleviates Alzheimer's disease-related plasticity and memory deficits. Nat Neurosci. Sep. 2013;16(9):1299-305. doi: 10.1038/nn.3486. Epub Aug. 11, 2013. (Author Manuscript, 22 pages).
Meyer-Schuman et al., Emerging mechanisms of aminoacyl-tRNA synthetase mutations in recessive and dominant human disease. Hum Mol Genet. Oct. 1, 2017;26(R2):R114-R127. doi: 10.1093/hmg/ddx231.
Niehues et al., Impaired protein translation in *Drosophila* models for Charcot-Marie-Tooth neuropathy caused by mutant tRNA synthetases. Nat Commun. Jul. 3, 2015;6:7520. doi: 10.1038/ncomms8520. Erratum in: Nat Commun. 2016;7:10497.
Extended European Search Report, mailed Jul. 1, 2022 for European Application No. 19876501.8.
Kapur et al., Regulation of mRNA Translation in Neurons—A Matter of Life and Death. Neuron. Nov. 1, 2017;96(3):616-637. doi: 10.1016/j.neuron.2017.09.057.
Mendonsa et al., Charcot-Marie-Tooth mutation in glycyl-tRNA synthetase stalls ribosomes in a pre-accommodation state and activates integrated stress response. Nucleic Acids Res. Sep. 27, 2021;49(17):10007-10017. doi: 10.1093/nar/gkab730.
Pakos-Zebrucka et al., The integrated stress response. EMBO Rep. Oct. 2016;17(10):1374-1395. doi: 10.15252/embr.201642195. Epub Sep. 14, 2016.
Spaulding et al., The integrated stress response contributes to tRNA synthetase-associated peripheral neuropathy. Science. Sep. 3, 2021;373(6559):1156-1161. doi: 10.1126/science.abb3414. Epub Sep. 1, 2021.

* cited by examiner

*Primary Examiner* — Sean McGarry
(74) *Attorney, Agent, or Firm* — Wolf, Greenfield & Sacks, P.C.

(57) ABSTRACT

Provided herein, in some embodiments, are methods and compositions for the treatment of Charcot-Marie-Tooth disease, comprising an inhibitor of a GCN2 pathway component.

10 Claims, 16 Drawing Sheets

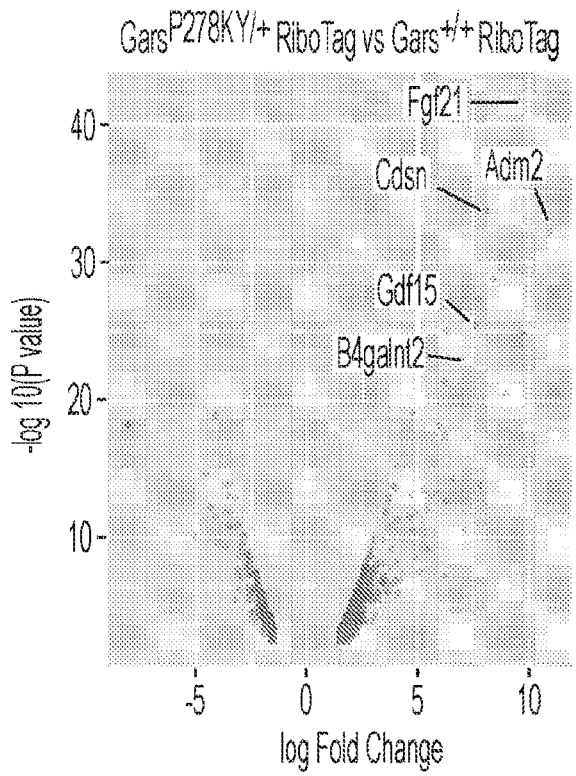

FIG. 2D

| Gars^C201R/+ motor neurons | PValue | Gars^P278KY/+ motor neurons | PValue | Gars^C201R/+ spinal cord | PValue | Gars^P278KY/+ spinal cord | PValue | Gars^delETAQ/+ spinal cord | PValue |
|---|---|---|---|---|---|---|---|---|---|
| Fgf21 | 7.3E-28 | Fgf21 | 1.4E-42 | Cfd | 1.4E-137 | Fgf21 | 6.1E-64 | Fgf21 | 1.2E-160 |
| Cdsn | 4.9E-26 | Cdsn | 1.6E-34 | Adipoq | 4.0E-130 | Cdsn | 2.7E-52 | Myh4 | 3.1E-103 |
| Atf4 | 2.7E-19 | Adm2 | 5.93E-33 | Fgf21 | 1.0E-128 | Adm2 | 8.2E-23 | Cdsn | 1.8E-90 |
| Gdf15 | 3.8E-19 | Cass4 | 1.6E-29 | Fabp4 | 1.8E-119 | Gdf15 | 9.7E-15 | P2rx3 | 2.2E-70 |
| Psph | 1.2E-18 | Fev | 4.6E-28 | Plin1 | 1.1E-81 | B4galnt2 | 1.9E-13 | B4galnt2 | 6.8E-47 |
| Phgdh | 7.1E-18 | Cox6a2 | 8.2E-26 | Cidec | 5.5E-78 | P2rx3 | 4.7E-07 | Plac9b | 1.1E-47 |
| Clic4 | 7.3E-18 | Gdf15 | 3.8E-26 | Ces1d | 8.5E-72 | Taf7l | 2.8E-07 | Duxbl1 | 1.6E-41 |
| B4galnt2 | 3.0E-17 | Ostn | 1.7E-25 | Cdsn | 1.5E-49 | Fev | 2.3E-05 | Fev | 7.7E-25 |
| Adm2 | 1.8E-16 | B4galnt2 | 1.4E-23 | B4galnt2 | 2.4E-20 | Steap1 | 1.6E-04 | Cass4 | 3.6E-23 |
| Cox6a2 | 1.8E-15 | Cyb5r2 | 5.0E-22 | Mup10 | 2.4E-20 | | | Mylk2 | 3.6E-23 |

FIG. 2E

TREATMENTS FOR CHARCOT-MARIE-TOOTH DISEASE

RELATED APPLICATIONS

This application is a national stage filing under 35 U.S.C. § 371 of international application number PCT/US2019/058045, filed Oct. 25, 2019, which claims the benefit of U.S. provisional application No. 62/751,388, filed Oct. 26, 2018, each of which is incorporated by reference herein in its entirety.

FEDERALLY-SPONSORED RESEARCH

This invention was made with government support under R01 NS054154 and R24 NS098523, awarded by National Institutes of Health. The government has certain rights in the invention.

BACKGROUND

Charcot-Marie-Tooth (CMT) disease, although a rare inherited peripheral neuropathy, is the most common inherited disease of the peripheral nervous system, resulting in the specific degeneration of peripheral motor and sensory axons (She, H., Clin Genet, 1974; 6(2): 98-1181; Saporta, M. A. et al. Neurol Clin, 2013; 31(2): 597-619). Mutations in at least 80-100 genes can lead to CMT in humans, and mutations in at least five tRNA synthetase genes (GARS (glycyl-tRNA synthetase), YARS (tyrosyl-tRNA synthetase), HARS (histidyl-tRNA synthetase), AARS (alanyl-tRNA synthetase), and WARS (tryptophanyl-tRNA synthetase)) account for approximately 10% of the dominant axonal (type 2) forms of CMT (CMT2). All patients are currently limited to palliative treatments.

SUMMARY

The present disclosure provides, in some aspects, methods and compositions for treating (e.g., alleviating the symptoms of) Charcot-Marie-Tooth (CMT) disease, including subtypes of CMT. While the mechanism by which mutations in GARS cause neurodegeneration is unclear, impaired translation has emerged as a potential toxic gain-of-function mechanism (Niehues, S., et al. Nat Commun, 2015). Indeed, all tRNA synthetases (ARSs) participate in translation, thus impairment in this process is an attractive disease mechanism. The experimental data provided herein shows, quite unexpectedly, that knockout of Gcn2 (also known as Eukaryotic Translation Initiation Factor 2 Alpha Kinase 4, EIF2AK4) in a validated CMT2D mouse model (Gcn2$^{-/-}$; Gars$^{P278KY/+}$) results in mice with increased body weights, improved grip strength, and motor nerve function closer to wild-type mice. This was particularly surprising because when mice with mutations causing defective translation elongation are crossed to Gcn2$^{-/-}$ mice, these double mutant mice show increased neurodegeneration and advanced disease progression (Ishimura, R., et al. Elife, 2016; 5). With these results in mind, and because it was thought that the integrated stress response likely activated through GCN2—would help motor neurons to cope with the stress induced by mutant GARS protein, the hypothesis was that Gcn2$^{-/-}$; Gars$^{P278KY/+}$ mice would exhibit increased neurodegeneration and die within days of birth. This, in fact, was not the case. Instead, these Gcn2$^{-/-}$; Gars$^{P278KY/+}$ mice exhibit significant alleviation of neuropathy.

Thus, some aspects of the present disclosure provide methods that include administering to a subject an inhibitor of expression and/or activity of a GCN2 pathway component, wherein the subject has a disease-associated mutation in a tRNA synthetase gene.

Other aspects of the present disclosure provide methods that include: administering to a subject that expresses a GCN2 pathway component an inhibitor of expression and/or activity of the GCN2 pathway component, wherein the subject comprise a disease-associated mutation in a tRNA synthetase gene; and assaying the mouse for an improvement in a symptom of Charcot-Marie-Tooth (CMT) disease and/or assaying the mouse for an adverse effect, relative to a control or relative to baseline.

Still other aspects of the present disclosure provide methods that include contacting a cell that expresses a GCN2 pathway component with an inhibitor of expression and/or activity of the GCN2 pathway component, wherein the cell comprises a disease-associated mutation in a tRNA synthetase gene.

Further aspects of the present disclosure provide methods that include administering to a subject an inhibitor of GCN2 expression and/or activity, wherein the subject has a disease-associated mutation in a tRNA synthetase gene.

Other aspects of the present disclosure provide methods that include administering to a Gars$^{P278KY/+}$ mouse an inhibitor of GCN2 expression and/or activity, and assaying the mouse for in improvement in a symptom of Charcot-Marie-Tooth (CMT) disease.

Still other aspects of the present disclosure provide methods that include contacting a cell that expresses GCN2 with an inhibitor of GCN2 expression and/or activity, wherein the cell comprises a disease-associated mutation in a tRNA synthetase gene.

BRIEF DESCRIPTION OF THE DRAWINGS

FIG. 2D shows ribosome-associated mRNA that is up-(log FC>1.5; p value<0.05) or downregulated (log FC<-1.5; p value<0.05) in Gars$^{P278KY/+}$ motor neurons compared to Gars$^{+/+}$. 633 genes are upregulated and 237 are downregulated. Analysis was performed on 4-5 animals per genotype at 8 weeks of age. FIG. 2E shows the top 10 upregulated transcripts based on p value significance. All bolded transcripts are present in at least 2 datasets. 3 males and 3 females per genotype at 8 weeks of age were used for each RNA sequencing experiment.

DETAILED DESCRIPTION

Figure 1A:
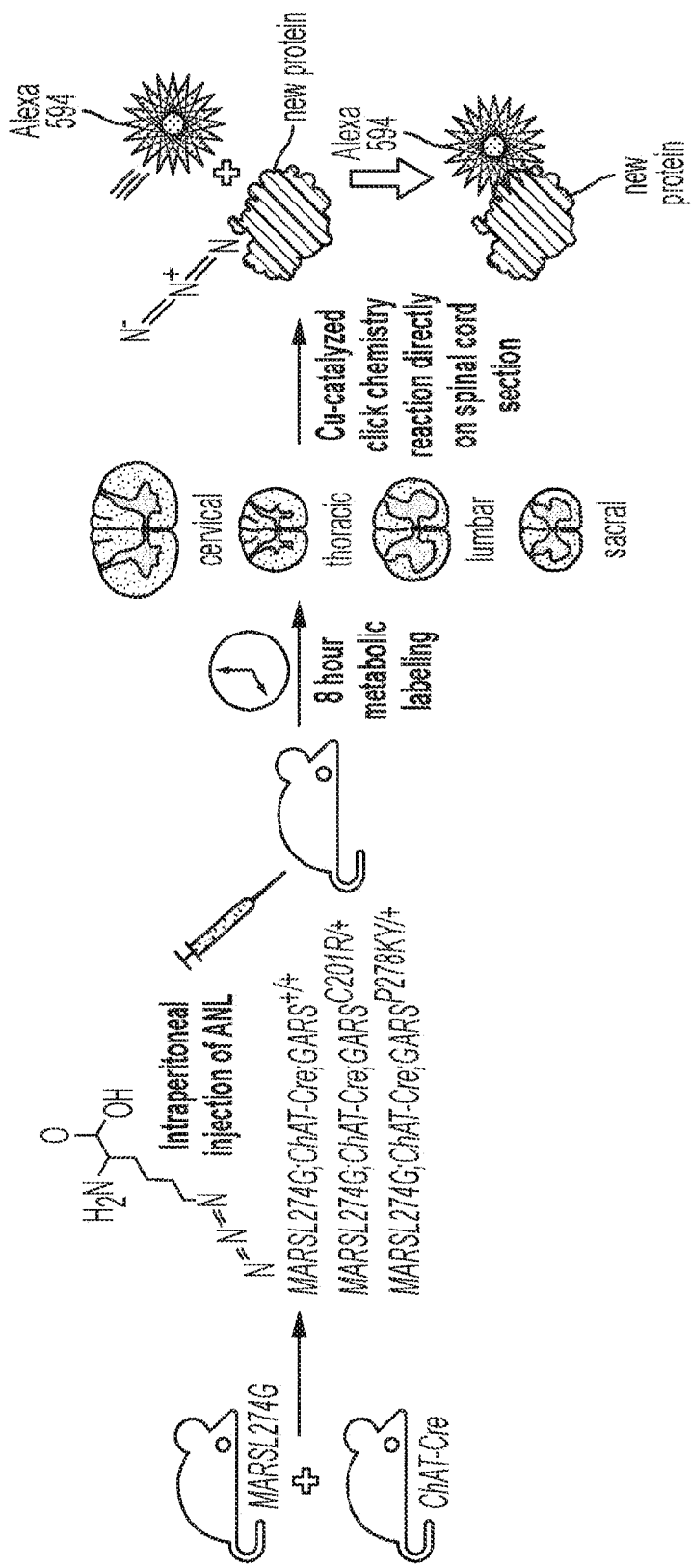
FIG. 1A shows an overview of the FUNCAT protocol. MARS$^{L274G}$; ChAT-Cre mice are injected with 400 mg/kg body weight ANL and metabolic labeling occurs for 8 hours. Cervical, thoracic, lumbar, and sacral regions of the spinal cord are then cryo-sectioned and copper-catalyzed click chemistry is performed directly on the slide. Proteins tagged with ANL react with alkyne-conjugated Alexa594 and are fluorescently labeled.

Charcot-Marie-Tooth disease (CMT) is a debilitating inherited peripheral neuropathy resulting in progressive distal muscle weakness, atrophy, and loss of sensation. CMT is genetically heterogeneous, with thousands of mutations in over 80 different genes leading to demyelinating or axonal forms. There are genetically similar subgroups, including the largest protein family implicated in the disease, the tRNA synthetases (ARSs). ARSs are the enzymes responsible for aminoacylation of tRNAs during translation and are therefore ubiquitously expressed and essential proteins. Dominant mutations in at least five ARSs cause axonal forms of CMT, including glycyl ARS (GARS), tyrosyl ARS (YARS), histidyl ARS (HARS), tryptophanyl ARS (WARS), and alanyl ARS (AARS). How mutations in ARSs cause CMT is unclear, however, the overall similar clinical presentation of patients suggests shared disease mechanisms.

Gene expression profiling in mouse models of Charcot-Marie-Tooth type 2D (CMT2D), caused by mutations in GARS, are consistent with the activation of the integrated stress response selectively in affected neuron populations (peripheral motor neurons). A similar gene expression signature was observed in mouse models of dominant intermediate CMT type C, caused by mutations in Yars. The differentially expressed genes were consistent with activation of the integrated stress response through GCN2, a kinase that is activated by factors such as metabolic stress, mitochondrial dysfunction, or amino acid starvation. The experiments provided herein were designed to test the role of GCN2 in the pathogenesis of CMT2D. A dominant Gars mutation that causes neuropathy in mice was bred into a GCN2 knockout background. The double mutant mice were in fact milder in their neuropathy symptoms than mice carrying only the Gars mutation. This indicates that activation of GCN2 contributes to the disease severity, and suggests that inhibitors (e.g., pharmacological inhibitors) of GCN2 would be beneficial in the treatment of CMT2D and other neuropathies associated with tRNA synthetase mutations.

Charcot-Marie-Tooth Disease

In some embodiments, a subject (e.g., a human subject) has Charcot-Marie-Tooth (CMT) disease, which encompasses a group of inherited peripheral neuropathies that are characterized by a slow, progressive degeneration of the muscles in the foot, lower leg, hand, and forearm, with a mild loss of sensation in the limbs, fingers, and toes. Roughly 125,000 people currently suffer from CMT in the United States. There is no cure for CMT, and the only therapies available are palliative care, physical therapy, and occupational therapy.

There are two clinical types of CMT: demyelinating (Type 1) and axonal (Type 2). For Type 1 (CMT1), the defect is in Schwann cells and myelination, and for Type 2 (CMT2), the defect is intrinsic to the peripheral neurons. In some embodiments, a subject undergoing therapy with a GCN2 inhibitor has CMT1. In other embodiments, a subject has CMT2.

In some embodiments, a subject undergoing therapy with a GCN2 inhibitor has CMT type 2D (CMT2D). CMT2D, also known as GARS-associated axonal neuropathy, is a type of CMT2 that is characterized by adolescent or early-adult onset bilateral weakness of the lower muscles of the arms and legs. Subjects with CMT2D are characterized by mutations in the GARS tRNA synthetase gene.

In some embodiments, a subject undergoing therapy with a GCN2 inhibitor has dominant intermediate CMT type C (diCMT). Subjects with diCMT have decreased motor nerve conduction and axonal nerve fibers severity that is intermediate between subjects with CMT1 and CMT2. diCMT is characterized by early onset (e.g., in the first two decades of life) distal leg and arm weakness and numbness. diCMT is associated with mutations in the YARS tRNA synthetase gene.

In some embodiments, a subject undergoing therapy with a GCN2 inhibitor has CMT type 2W (CMT2W). CMT2W is a type of CMT2 that is characterized by mutations in the HARS tRNA synthetase gene and peripheral neuropathy that mainly affects the lower limbs, resulting in difficulty walking and distal sensory impairment. Some subjects with CMT2W also experience upper limb weakening. The age of onset of CTM2W symptoms is highly variable, ranging from childhood to late adulthood.

In some embodiments, a subject undergoing therapy with a GCN2 inhibitor has CMT type 2N. (CMT2N). CMT2N is a type of CMT2 that is characterized by mutations in the AARS tRNA synthetase gene and peripheral neuropathy that affects the lower limbs, resulting in difficulty standing, foot deformities, and muscle atrophy of the lower limbs. The age of onset of CMT2N symptoms is variable, ranging from early to late adulthood.

Transfer RNA Synthetases

In some embodiments, a subject has a disease-associated mutation in a transfer RNA (tRNA) synthetase gene. A disease-associated mutation is a mutated allele encoding a protein associated with (e.g., is a cause of and/or contributes to progression of) a disease.

As used herein, a tRNA synthetase is an enzyme that catalyzes the first step in protein translation by conjugating an amino acid onto its corresponding tRNA. In humans, there are 37 different tRNA synthetase enzymes, typically two for each amino acid, one functioning in cytosolic tRNA charging, and one functioning in mitochondrial tRNA charging. Two, GARS and KARS, are bifunctional in both the cytosol and mitochondrial translation, and one, EPRS, is a fusion of glutamic acid and proline tRNA synthetases expressed from a single gene. Additionally, tRNA synthetase enzymes act in tRNA proof-reading and export, cell signaling, DNA binding, transcriptional regulation, and RNA-dependent amino acid editing.

Aberrant tRNA synthetase expression and/or activity is associated with various disease states, including neuropathies such as CMT disease and distal spinal muscular atrophy type V, as well as auto-immune disorders including chronic myopathies, interstitial lung diseases, and polymyositis.

In some embodiments, the tRNA synthetase gene is glycyl-tRNA synthetase (GARS) (Gene ID: 2617 (human) or Gene ID: 353172 (mouse)). The GARS tRNA synthetase protein catalyzes the conjugation of glycine to its corresponding tRNA$^{Gly}$. The peripheral nerve diseases CMT2D and distal spinal muscular atrophy type V (dSMA-V) are linked to mutations in GARS. Non-limiting disease-associated mutations in human GARS include A111V (CMT2D), E125G (CMT2D and dSMA-V), D200Y (CMT2D), M292R (CMT2D), G294R (CMT2D), P298L (CMT2D), I334F (CMT2D), D554N (CMT2D), and G652A (CMT2D). Non-limiting disease-associated mutations in mouse GARS include P278KY (CMT2D), and C201R (CMT2D). In some embodiments, a human subject has a A111V, E125G, D200Y, M292R, G294R, P298L, I334F, D554N, and/or a G652A mutation in a GARS gene.

In some embodiments, the tRNA synthetase gene is tyrosyl-tRNA synthetase (YARS) (Gene ID: 8565 (human) or Gene ID: 107271 (mouse)). The YARS tRNA synthetase protein catalyzes the conjugation of tyrosine to its corresponding tRNA$^{Tyr}$. Non-limiting disease-associated mutations in human YARS include G41R (diCMTC), 153del156 (diCMTC), and E196K (diCMTC). A non-limiting disease-associated mutation in mouse YARS is E196K. In some embodiments, a human subject has a G41R, 153del156, and/or E196K mutation in a YARS gene.

In some embodiments, the tRNA synthetase gene is alanyl-tRNA synthetase (AARS) (Gene ID: 16, (human) or Gene ID: 234734 (mouse)). The AARS tRNA synthetase protein catalyzes the conjugation of alanine to its corresponding tRNA$^{Ala}$. CMT2N is linked to mutations in AARS. Non-limiting disease-associated mutations in human AARS include R329H (CMT2N) and N71Y (CMT2N). Non-limiting disease-associated mutations in mouse AARS include A448Q (CMT2N) and C723A (CMT2N). In some embodiments, a human subject has a R239H and/or N71Y mutation in a AARS gene.

In some embodiments, the tRNA synthetase gene is histidyl-tRNA synthetase (HARS) (Gene ID: 3035 (human) or Gene ID: 15115 (mouse)). The HARS tRNA synthetase protein catalyzes the conjugation of histidine to its corresponding tRNA$^{His}$. CMT2W is linked to mutations is HARS. Non-limiting disease-associated mutations in human HARS include: T132I (CMT2W), P134H (CMT2W), R137Q (CMT2W), D175E (CMT2W), V238A (CMT2W), D364Y (CMT2W), and P505S (CMT2W). In some embodiments, a human subject has a T132I, P134H, R137Q, D175E, V238A, D364Y, and/or P505S mutation in a HARS gene.

In some embodiments, the tRNA synthetase gene is tryptophanyl-tRNA synthetase (WARS) (Gene ID: 7453 (human) or Gene ID: 22375 (mouse)). The WARS tRNA synthetase protein catalyzes the conjugation of tryptophan to its corresponding tRNA$^{Trp}$. The peripheral nerve disease distal hereditary motor neuronopathy type IX is associated with a H257R mutation in the WARS gene. In some embodiments, a human subject has a H257R mutation in WARS gene.

Other tRNA synthetase alleles are encompassed by the present disclosure.

Methods of Treatment

Provided herein, in some embodiments, are methods of treating Charcot-Marie-Tooth disease (CMT) is a subject (e.g., a human subject), the method comprising, for example, administering to the subject an inhibitor of expression and/or activity of the GCN2 pathway component, wherein the subject has a disease-associated mutation in a tRNA synthetase gene.

A subject herein may be a mammalian subject, such as a human subject. In some embodiments, a subject is a non-human primate or a rodent (e.g., mouse or rat), for example, used as animal models.

Non-limiting examples of routes of administration include oral (e.g., tablet, capsule, or liquid), intravenous, subcutaneous, inhalation, intranasal, intrathecal, intramuscular, intraarterial, and intraneural.

In some embodiments, a therapeutically effective amount of an inhibitor may be administered to a subject to treat CMT. The term treat, as known in the art, refers to the process of alleviating at least one symptom associated with a disease (e.g., CMT). A symptom may be a physical, mental, or pathological manifestation of the disease. Symptoms associated with CMT, for example, are described elsewhere herein and include, among other things, various motor neuron dysfunctions. To treat CMT, an inhibitor of expression and/or activity of the GCN2 pathway component (e.g., GCN2) as provided herein should be administered in a therapeutically effective amount, which can be any amount used to treat CMT. Thus, in some embodiments, a therapeutically effective amount is an amount used to alleviate a symptom associated with CMT. Methods are known for determining a therapeutically amounts of various therapeutic molecules (e.g., inhibitors of expression and/or activity of GCN2 pathway components).

The GCN2 inhibitor may be administered to a subject as a single dose or as multiple doses over the course of days, weeks, months, or years. The dose/dosage of a GCN2 inhibitor may be determined by a skilled medical practitioner, taking into consideration one or more factors, such as type and severity of disease as well as subject age, weight, height, sex, and ethnicity.

Inhibitors of GCN2 Pathway Components

In some embodiments, an inhibitor of expression and/or activity of a GCN2 pathway component (a "GCN2 pathway inhibitor") is administered to a subject. A GCN2 pathway component is an any polynucleotide (e.g., DNA or RNA, e.g., a gene or gene transcript) or polypeptide (e.g., protein or peptide) in the GCN2 signaling pathway. In some embodiments, a GCN2 pathway inhibitor inhibits (directly or indirectly) expression and/or activity of GCN2. In some embodiments, a GCN2 pathway inhibitor inhibits (directly or indirectly) expression and/or activity of Activating Transcription Factor 4 (ATF4). In some embodiments, a GCN2 pathway inhibitor inhibits (directly or indirectly) expression and/or activity of a gene target of ATF4. Non-limiting examples of ATF4 gene targets include fibroblast growth factor 21 (Fgf21), growth differentiation factor 15 (Gdf15), adrenomedullin 2 (Adm2), corneodesmosin (Cdsn), and Beta-1,4-N-Acetyl-Galactosaminyltransferase 2 (B4galnt2). Other ATF4 gene targets are contemplated herein.

Expression of a gene is considered "inhibited" if the level of mRNA and/or protein encoded by the gene is reduced by at least 10% (e.g., at least 20%, 30%, 40%, 50%, 60%, 70%, 80%, 90%, or 100%) relative to a control (e.g., wild-type/unmodified expression of the same gene exposed to otherwise similar conditions). In some embodiments, an inhibitor of GCN2 expression reduces GCN2 expression by 10% to 100%. For example, an inhibitor of GCN2 expression may reduce GCN2 expression by 10-90%, 10-80%, 10-70%, 10-60%, 10-50%, 20-90%, 20-80%, 20-70%, 20-60%, 20-50%, 30-90%, 30-80%, 30-70%, 30-60%, 30-50%, 40-90%, 40-80%, 40-70%, 40-60%, 40-50%, 50-90%, 50-80%, 50-70%, 50-60%, 60-90%, 60-80%, 60-70%, 70-90%, 70-80%, 80-90%, or 90-100% relative to a control. Methods of measuring mRNA and/or protein levels are known (e.g., quantitative polymerase chain reaction (qPCR), Western blot analysis, microarray analysis, and reverse transcription polymerase chain reaction (RT-PCR)).

Activity of a gene is considered "inhibited" if the effect of the protein encoded by the gene on downstream targets/processes is reduced by at least 10% relative to a control. For example, inhibiting GCN2 protein activity, in some embodiments, reduces the level of phosphorylation of downstream targets, such as eIF2α and/or SREBP-1c. In some embodiments, an inhibitor of GCN2 activity reduces GCN2 activity by 10% to 100%. For example, an inhibitor of GCN2 activity may reduce GCN2 activity by 10-90%, 10-80%, 10-70%, 10-60%, 10-50%, 20-90%, 20-80%, 20-70%, 20-60%, 20-50%, 30-90%, 30-80%, 30-70%, 30-60%, 30-50%, 40-90%, 40-80%, 40-70%, 40-60%, 40-50%, 50-90%, 50-80%, 50-70%, 50-60%, 60-90%, 60-80%, 60-70%, 70-90%, 70-80%, 80-90%, or 90-100% relative to a control. Methods of measuring protein activity levels are known (e.g., Western blot analysis of downstream targets, such as phosphorylated eIF2α and Western blot analysis of phosphorylated SREBP-1c).

The GCN2 gene (general control nonderepressible 2) (Gene ID: 440275 (human) or Gene ID: 27103 (mouse)) is a serine/threonine kinase protein that modulates amino acid metabolism in a subject in response to nutrient deprivation through binding to an uncharged transfer RNA (tRNA). GCN2 regulates the integrated stress response pathway, which inhibits protein synthesis under conditions of amino acid deprivation by phosphorylating and down-regulating the activity of the kinase eIF2α. This down-regulation of eIF2α by GCN2 diminishes translation and protein production, while simultaneously up-regulating the expression of stress-related target genes. Additionally, GCN2 decreases the expression of the transcription factor SREBP-1c and thereby decreases fatty acid and triglyceride synthesis following leucine deprivation.

In some embodiments, the inhibitor of GCN2 expression and/or activity is a polypeptide (e.g., protein or peptide). Non-limiting examples of proteins that may be used as provided herein includes programmable nucleases and antibodies.

Non-limiting examples of programmable nucleases include zinc-finger nucleases (ZFNs), transcription activator-like effector nucleases (TALENs) and RNA-guided engineered nucleases (RGENs) derived from the bacterial clustered regularly interspaced short palindromic repeat (CRISPR)-Cas (CRISPR-associated) system. See, e.g., Joung J K et al. *Nat Rev Mol Cell Biol.* 2013; 14(1):49-55; Carroll D *Genetics.* 2011; 188(4): 773-782; Gaj T et al. *Trends Biotechnol.* 2013; 31(7):397-405; Jinek et al., *Science*, 337, 816-821 (2012); and Deltcheva et al., *Nature*, 471, 602-607 (2011).

These programmable nucleases enable targeted genetic modifications in cells. ZFNs and TALENs are composed of DNA-binding proteins and the FokI nuclease domain. RGENs are derived from the type II CRISPR-Cas adaptive immune system in bacteria and are composed of guide RNAs and a Cas protein (or homolog, ortholog, or variant thereof, or nickase derivative thereof). Examples of RGENs include, without limitation, Cas9, Cas3, Cas10, and Cpf1.

Non-limiting examples of antibodies include monoclonal antibodies, polyclonal antibodies, single chain fragment antibodies (scFvs), Nanobodies®, affibodies, diabodies, triabodies, and tetrabodies. An antibody may be a human antibody, a humanized antibody, or a chimeric antibody. In some embodiments, an antibody binds to an epitope of a GCN2 protein to inhibit GCN2 activity.

In some embodiments, the inhibitor of GCN2 expression and/or activity is a polynucleotide (e.g., RNA or DNA). Non-limiting examples of polynucleotides include RNA interference molecules and antisense RNA molecules.

RNA interference refers to a biological process by which RNA molecules inhibit gene expression by binding target DNA molecules and inhibiting transcription, or by binding messenger RNA (mRNA) molecules and inhibiting translation. Non-limiting examples of RNA interference molecules that may be used as provided herein include microRNAs (miRNAs), small interfering RNAs (siRNAs), and short hairpin RNAs (shRNAs), which bind to and inhibit expression of a gene associated with an inherited peripheral neuropathy (e.g., GCN2). In some embodiments, a RNA interference molecule inhibits GCN2 expression and/or activity by binding to GCN2 and blocking transcription or promoting degradation of the GCN2 mRNA.

Antisense RNA molecules are single-stranded RNA oligonucleotides that bind a nucleic acid that encodes a polypeptide, thereby inhibiting transcription and translation of that polypeptide. Non-limiting examples of antisense RNA molecules include short non-coding RNAs (<200 nucleotides) and long non-coding RNAs (>200 nucleotides). In some embodiments, the antisense RNA molecules bind to and inhibit expression of a gene associated with an inherited peripheral neuropathy (e.g., GCN2). In some embodiments, an antisense RNA molecule inhibits GCN2 expression by binding to and preventing expression of GCN2.

In some embodiments, the inhibitor of GCN2 expression is a small molecule drug. A small molecule drug is a low molecular weight (e.g., less than or equal to 900 daltons) substance that enters cells, where it can affect other molecules such as proteins and nucleic acids. In some embodiments, the small molecule drug is selected from A-92 (triazolo[4,5-d]pyrimidine derivative), indirubin-3-monoxime, SP600125, and spleen tyrosine kinase (Syk) inhibitors.

In some embodiments, a small molecule drug is the GCN2 inhibitor A-92. A-92 is a traizolopyrimidine derivative described in WO 2013/110309 A1. In some embodiments, the amount of A-92 administered is between 0.1 mg/kg-100 mg/kg. In some embodiments, the amount of A-92 administered is between 0.1 mg/kg and 10 mg/kg. In some embodiments, the amount of A-92 administered is 0.1 mg/kg, 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, or 100 mg/kg.

In some embodiments, a small molecule drug is the kinase inhibitor indirubin-3-monoxime. Indirubin-3-monoxime is an indoline small molecule that reversibly inhibits the proliferation of cells. In some embodiments, the amount of indirubin-3-monoxime administered is between 0.1 µM-100 µM. In some embodiments, the amount of indirubin-3-monoxime administered is between 0.1 µM and 10 µM. In some embodiments, the amount of indirubin-3-monoxime administered is 0.1 µM, 0.5 µM, 1.0 µM, 1.5 µM, 2.0 µM, 2.5 µM, 3. µM, 3.5 µM, 4.0 µM, 4.5 µM, 5.0 µM, 5.5 µM, 6.0 µM, 6.5 µM, 7.0 µM, 7.5 µM, 8.0 µM, 8.5 µM, 9.0 µM, 9.5 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, or 100 µM.

In some embodiments, a small molecule drug is the kinase inhibitor SP600125. SP600125 is an anthrapyrazolone kinase inhibitor that competes with ATP to inhibit kinase phosphorylation and activation. In some embodiments, the amount of SP600125 administered is between 0.1 µM-100 µM. In some embodiments, the amount of SP600125 administered is between 0.1 µM and 10 µM. In some embodiments, the amount of SP600125 administered is 0.1 µM, 0.5 µM, 1.0 µM, 1.5 µM, 2.0 µM, 2.5 µM, 3. µM, 3.5 µM, 4.0 µM, 4.5 µM, 5.0 µM, 5.5 µM, 6.0 µM, 6.5 µM, 7.0 µM, 7.5 µM, 8.0 µM, 8.5 µM, 9.0 µM, 9.5 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, or 100 µM.

In some embodiments, a small molecule drug is a Syk inhibitor. Syk protein is a kinase that is predominantly expressed in hematopoietic cells such as B cells. Syk transmits activating signals from the B cell receptor and constitutively active Syk activity can transform B cells. Non-limiting examples of Syk inhibitors include: GS-9973 (Entospletinib), R788 (Fostamatinib, Tavalisse®) and Nilvadipine. In some embodiments, the amount of Syk inhibitor administered is between 0.1 µM-100 µM. In some embodiments, the amount of Syk inhibitor administered is between 0.1 µM and 10 µM. In some embodiments, the amount of Syk inhibitor administered is 0.1 µM, 0.5 µM, 1.0 µM, 1.5 µM, 2.0 µM, 2.5 µM, 3. µM, 3.5 µM, 4.0 µM, 4.5 µM, 5.0 µM, 5.5 µM, 6.0 µM, 6.5 µM, 7.0 µM, 7.5 µM, 8.0 µM, 8.5 µM, 9.0 µM, 9.5 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, or 100 µM.

In some embodiments, administration of an inhibitor of GCN2 expression and/or activity results in an improvement in body weight, grip strength, and/or motor neuron function in the subject. In some embodiments, an improvement is an at least 20% (e.g., 20%, 30%, 40%, 50%, 60%, 70%, 80%, 90%, or 100%) improvement, relative to baseline (e.g., within 1-7 days prior to receiving treatment).

Screening Methods

Also provided herein are methods for identifying clinical candidates (e.g., agents such as polypeptides, polynucleotides, and/or small molecule drugs) that may be used to treat CMT disease/disease subtypes.

In some embodiments, the methods comprising administering to a subject that expresses a GCN2 pathway component an inhibitor of expression and/or activity of the GCN2 pathway component, wherein the subject comprise a disease-associated mutation in a tRNA synthetase gene, and assaying the mouse for an improvement in a symptom of Charcot-Marie-Tooth (CMT) disease and/or assaying the mouse for an adverse effect, relative to a control or relative to baseline.

The subject, in some embodiments, is a rodent. For example, the rodent may be a mouse or a rat.

In some embodiments, the methods comprise administering to a Gars mutant mouse model an inhibitor of GCN2 expression or activity, and assaying the mouse (1) for an improvement in a symptom of Charcot-Marie-Tooth (CMT) disease and/or (2) for an adverse effect (e.g., toxicity, morbidity, mortality, alteration in body weight, levels of enzymes, loss of function, or pathological change detected at the microscopic, macroscopic or physiological level).

Toxicity may be assessed, for example, by observing physical or mental signs of illness.

A Gars mutant mouse model, in some embodiments, is a Gars$^{P278KY+}$ mouse, a Gars$^{C201R/+}$ mouse, or a Gars$^{DelETAQ/+}$ mouse. A Yars mutant mouse model, in some embodiments, is a Yars$^{E196K/E196K}$ mouse.

Symptoms of CMT disease in mice include reduced body weight, decreased grip strength, decreased motor nerve function, foot deformities, and abnormal gait, relative to control mice (e.g., wild-type mice). Thus, an assay for an improvement in a symptom of CMT may include measuring and/or characterizing body weight, grip strength, motor nerve function, foot deformities, and/or abnormal gait. Other symptoms and adverse effects (side effects) may be assessed.

In some embodiments, a screening method comprising contacting a cell that expresses a GCN2 pathway component with an inhibitor of expression and/or activity of the GCN2 pathway component, wherein the cell comprises a disease-associated mutation in a tRNA synthetase gene. In some embodiments, the cell is a motor neuron.

In some embodiments, an agent is identified as a clinical candidate if body weight, grip strength, and/or motor neuron function is improved in the subject by at least 20% following administration of the inhibitor of GCN2 expression and/or activity, relative to a control or relative to baseline.

A control may be an untreated subject or a subject treated with only buffer or other inert substance. Baseline, as is known in the art, is the state of a particular condition in a subject prior to administration of the particular therapy (e.g., within 1 to 3 months).

EXAMPLES

Because all ARSs participate in translation, impairment in this process is an attractive disease mechanism to test in mammalian models of tRNA synthetase-associated CMT. To this end, we have performed in vivo, cell type-specific translational and transcriptional profiling in motor neurons of three well-established mouse models of Charcot-Marie-Tooth type 2D (CMT2D). This profiling revealed impaired translation in mutant Gars motor neurons and the selective activation of the integrated stress response (ISR) in the largest motor and sensory peripheral neurons. Activation of the ISR occurs through the translational homeostasis-sensing kinase, GCN2, indicating that GCN2 could be responding to impairments in translation. Genetic removal of GCN2 kinase significantly alleviates mutant Gars neuropathy, suggesting that chronic activation of the ISR contributes to CMT2D. The ISR is also activated in motor neurons of mice with mutations in Yars, a model of dominant intermediate CMT type C. Together, these data support impairments in translation as a toxic gain-of-function disease mechanism in mice with dominant mutations in Gars and Yars.

Example 1. Translation is Impaired in Mutant Gars Motor Neurons

We performed our first translational profiling experiments in two well-established CMT2D mouse models, the relatively mild Gars$^{C201R/+}$, and the more severe Gars$^{P278KY/+}$ (Achilli et al. 2009a; Seburn et al. 2006). To evaluate translation in motor neurons in vivo, we performed fluorescent non-canonical amino acid-tagging (FUNCAT), a technique which allows for the visualization and quantification of newly synthesized protein. A mouse engineered to express a Cre-inducible form of bacterial methionyl-ARS (MARS$^{L274G}$), which loads the methionine analog, azidonorleucine (ANL), onto cognate tRNA was crossed to the choline acetyltransferase-Cre (ChAT-Cre) driver mouse line to induce transgene expression in motor neurons (Alvarez-Castelao et al. 2017). Unlike methionine, ANL contains an azide group which undergoes copper catalyzed azide-alkyne cycloaddition in the presence of an alkyne-conjugated substrate. ANL was delivered as an intraperitoneal injection of 400 mg/kg body weight in MARS$^{L274G}$; ChAT-Cre mice on a Gars$^{+/+}$, Gars$^{P278KY/+}$ or Gars$^{C201R/+}$ background. Following 8 hours of ANL incorporation into proteins, the copper-catalyzed cycloaddition reaction was performed using an alkyne-conjugated fluorophore directly on spinal cord sections, and intensity of fluorescence quantitatively measures abundance of newly translated protein in motor neurons (FIG. 1A).

Figure 1B:
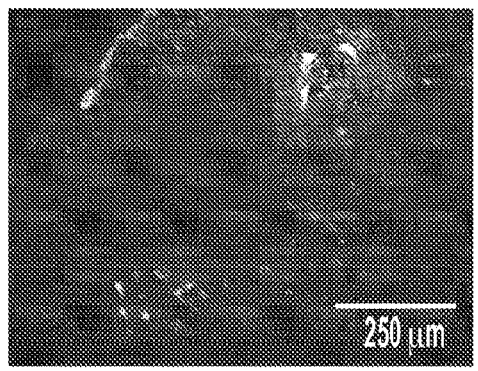
FIG. 1B shows that within the spinal cord FUNCAT labeling is specific to motor neurons of the ventral horn. 10× image.
Figure 1C:
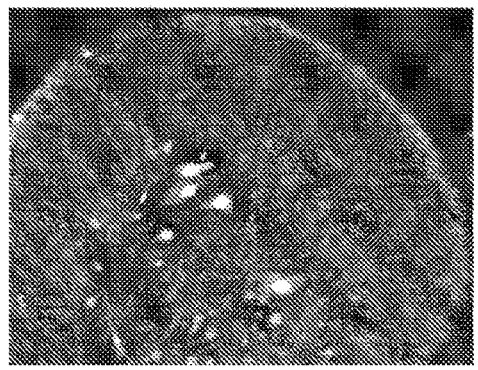
FIG. 1C shows the newly synthesized protein in Gars+$^{4}$ sacral motor neurons. 20× image.
Figure 1D:
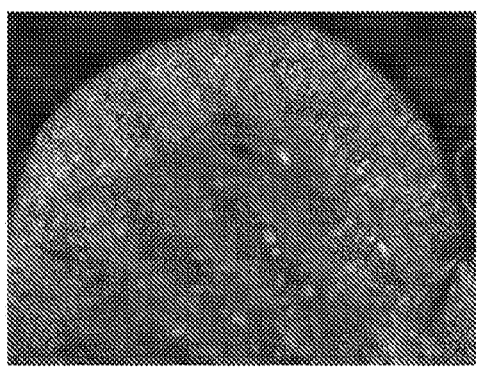
FIG. 1D shows the newly synthesized protein in Gars$^{C201R/+}$ sacral motor neurons. 20× image.
Figure 1E:
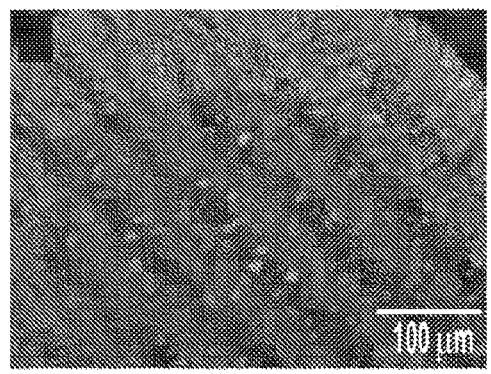
FIG. 1E shows the newly synthesized protein in Gars$^{P278KY/+}$ sacral motor neurons. 20× image. Scale bar in FIG. 1E also applies to FIGS. 1C and 1D.
Figure 1F:
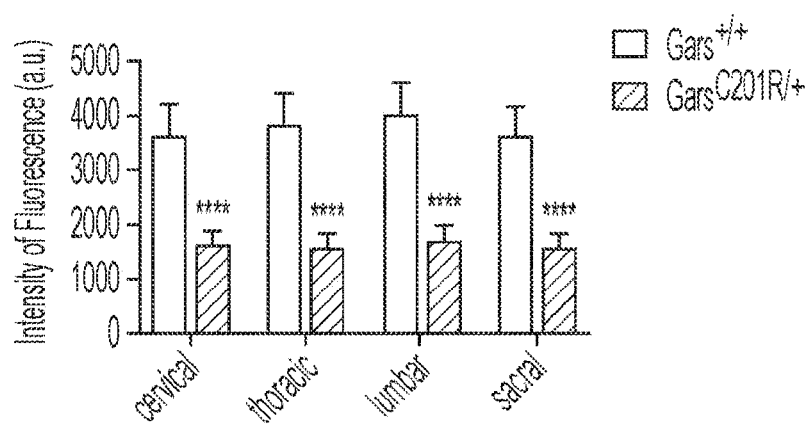
FIG. 1F shows that translation, as represented by intensity of fluorescence, is decreased in Gars$^{C201R/+}$ motor neurons by approximately 55-60% compared to Gars$^{+/+}$.
Figure 1G:
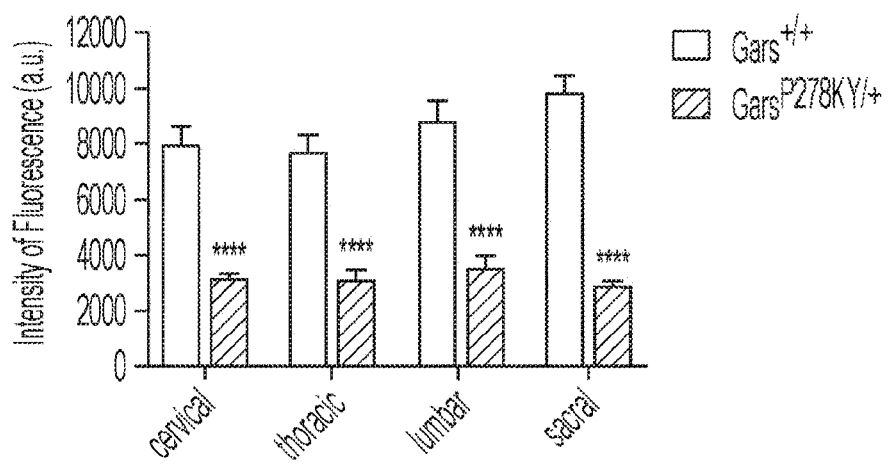
FIG. 1G shows that translation is decreased by approximately 60% in Gars$^{P278KY/+}$ cervical, thoracic, and lumbar motor neurons, and by approximately 70% in sacral motor neurons. Analysis was performed on 3 females and 3 males per genotype at 8 weeks of age. Values in FIGS. 1F and 1G are the sum of fluorescence for all 6 animals per genotype±SD. *****=p<0.0001.

ANL incorporation in Gars$^{+/+}$ spinal cord is specific to motor neurons of the ventral horn (FIG. 1B), with the exception of ChAT-expressing pre-sympathetic ganglionic neurons in thoracic sections that can be easily distinguished from motor neurons (not shown). Thus, abundance of newly translated protein can be measured reliably in motor neuron populations of cervical, thoracic, lumbar, and sacral spinal cord. At 8 weeks of age, well past disease onset in both CMT2D models, Gars$^{C201R/+}$ and Gars$^{P278KY/+}$ motor neurons show reduced fluorescence compared to Gars in all regions of the spinal cord (FIGS. 1C-1E). The milder Gars$^{C201R/+}$ mouse model showed a 55-60% reduction in all motor neuron populations (FIG. 1F). The more severe Gars$^{P278KY/+}$ showed a 60% reduction in cervical, thoracic, and lumbar motor neurons, and a 70% reduction in sacral motor neurons (FIG. 1G). These results indicate that translation is severely impaired in Gars$^{C201R/+}$ and Gars$^{P278KY/+}$ motor neurons.

To determine if translation is also impaired pre-disease onset, we performed FUNCAT in 2 week-old Gars$^{C201R/+}$ mice, a time just before any overt signs of neuropathy are evident. Although there are trends of reduced fluorescence in all Gars$^{C201R/+}$ motor neuron populations, none has a reduction that amounts to a statistical difference from Gars (data not shown). These data indicate that impairments in translation are just starting to manifest at this early timepoint, and could correlate with disease onset.

Because mutant Gars is expressed in every cell type of the body, we asked if translation is impaired in other tissue types unaffected by disease. To measure translation in the liver and heart we turned to puromycin labeling. Puromycin is a bacterial metabolite that structurally resembles an amino-acylated tRNA. Incorporation into nascent polypeptide chains causes translation termination, and blotting with a puromycin antibody provides a quantitative measure of translation. We injected mice with 60 mg/kg body weight puromycin and allowed it to incorporate into nascent polypeptides for 1 hour. Mice treated with puromycin show a smear of anti-puromycin-labeled protein in tissues, while untreated mice show no smear (data not shown). We were unable to find evidence of impaired translation in liver or heart tissue of Gars$^{P278KY/+}$ or Gars$^{C201R/+}$ mice, or in Gars$^{delETAQ/+}$ mice that contain a mutation found in a young CMT2D patient (data not shown) (Morelli, et al; submitted 2019). These experiments indicate that in mice, impairments in translation are restricted to cell types affected by disease.

Figure 2A:
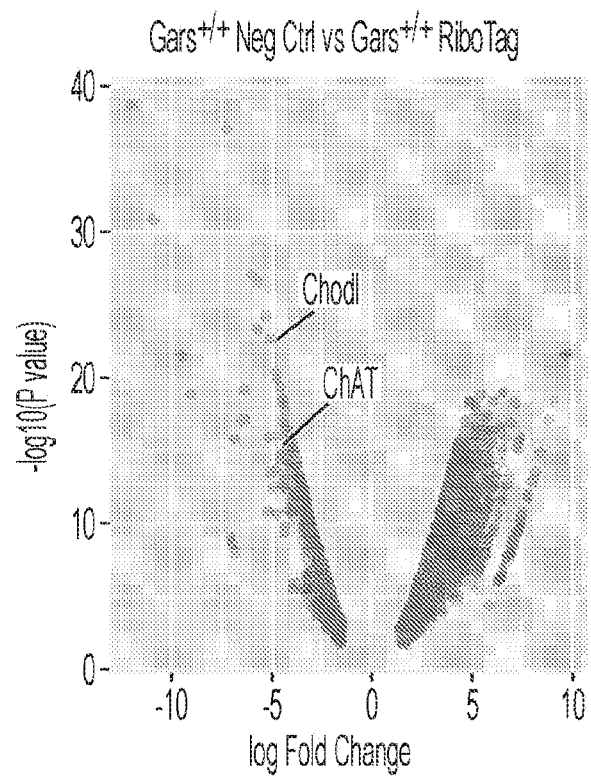
FIG. 2A shows ribosome-associated mRNA enriched in Gars$^{+/+}$ motor neurons vs the whole spinal cord. Genes plotted have a log FC 11.51, FDR<0.05 and p value<0.05. There are 1907 enriched genes in motor neurons (log FC<−1.5; p value<0.05) and 3725 genes enriched in nonmotor neuron cell types of the spinal cord (log FC>1.5; p value<0.05). Analysis was performed on 4-5 animals per genotype at 8 weeks of age.

Example 2. Motor Neuron Translational and Transcriptional Gene Expression Signatures are Shared Among Multiple Gars Alleles, Including the Human Mutation, Gars$^{delETAQ/+}$ To determine which mRNA species are undergoing differential translation in mutant Gars motor neurons we performed in vivo ribosome-tagging (RiboTagging). RiboTag mice contain a transgene consisting of a loxP-flanked, triple HA-tagged ribosomal protein, RPL22 (Sanz et al. 2009). When used in combination with ChAT-Cre, HA-RPL22 can be immunoprecipitated from motor neurons with anti-HA antibody and the mRNA presumably undergoing active translation at the ribosome is eluted and sequenced. When mRNA immunoprecipitated from Gars$^{+/+}$; HA-RPL22; ChAT-Cre spinal cords is compared to nonspecific mRNA immunoprecipitated from no-Cre controls, motor neuron-enriched mRNA encompassed 1,907 transcripts, including the well-known markers ChAT (enriched 15-fold) and chondrolectin (Chodl) (enriched 33 fold), as well as additional markers of projection neurons including neurofilament heavy, medium, and light chains (Nefh, Nefm, Nefl) (enriched ~6, 8, and 9-fold, respectively). In contrast, the 3,725 transcripts more abundant in nonspecific spinal cord pull-downs are correspondingly de-enriched in motor neurons, and include the astrocytic marker glial fibrillary acid protein (GFAP) (de-enriched ~4-fold) and the oligodendrocytic markers myelin oligodendrocyte protein (mog) (de-enriched ~3-fold) and myelin associated protein (mag) (de-enriched ~4-fold) (FIG. 2A).

Figure 2B:
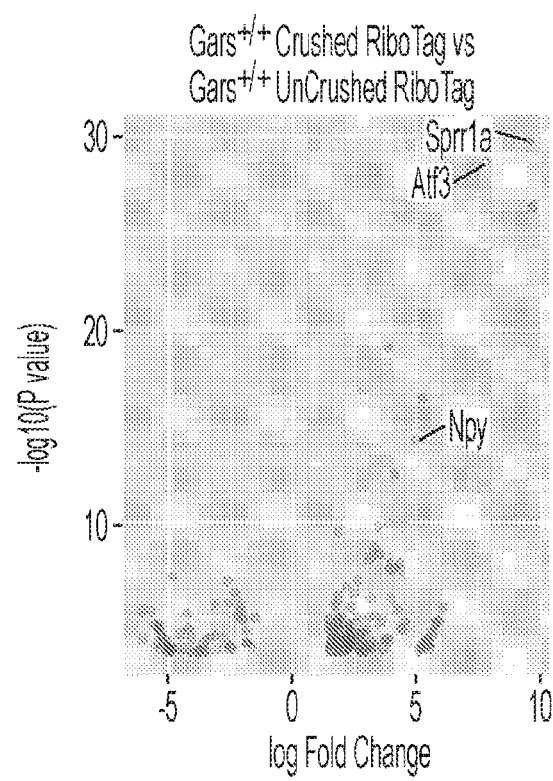
FIG. 2B shows ribosome-associated mRNA that is up- or downregulated in Gars$^{+/+}$ motor neurons 4 days after unilateral sciatic nerve crush. 144 genes are upregulated (log FC>1.5; p value<0.05) and 68 are downregulated (log FC<-1.5; p value<0.05). Analysis was performed on 2 animals per condition at 8 weeks of age.

As an additional test of the reliability of RiboTagging, as well as to provide a disease-relevant comparison to mutant Gars motor neurons, we sequenced ribosome associated mRNA from Gars$^{+/+}$ motor neurons of the spinal cord 4 days after unilateral sciatic nerve crush. 144 transcripts were upregulated and 68 downregulated in Gars$^{+/+}$ motor neurons after nerve crush compared to those from Gars$^{+/+}$ mice that had not undergone the crush surgery (FIG. 2B). Among the top 10 upregulated transcripts after crush were small proline-rich repeat protein 1A (Sprr1a), activating transcription factor 3 (Atf3), and neuropeptide tyrosine (Npy), all known to be markers of regeneration in peripheral neurons after injury (Starkey et al. 2009; Linda, Skold, and Ochsmann 2011; Zhang et al. 1993). These experiments confirm reliability of the RiboTagging technique, as well as create a complete catalog of motor neuron ribosome-associated mRNA following sciatic nerve crush for comparison against mutant Gars.

Figure 2C:
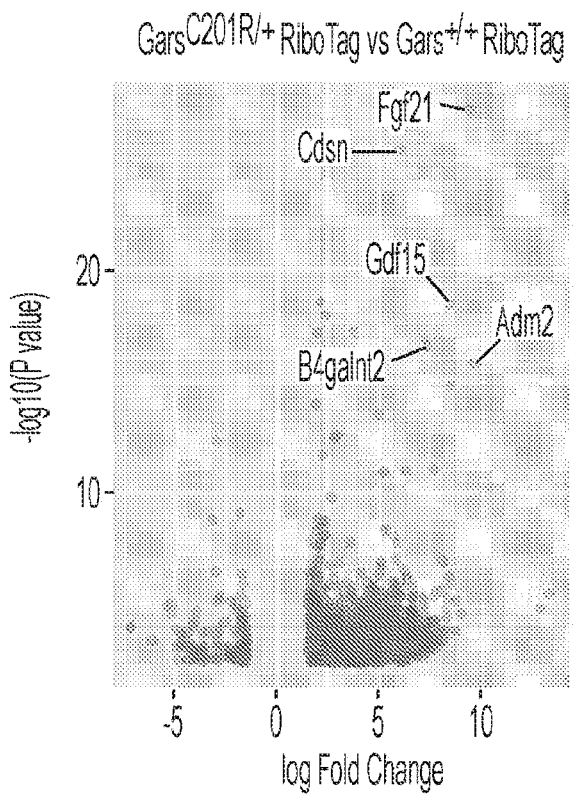
FIG. 2C shows ribosome-associated mRNA that is up- or downregulated in Gars$^{C201R/+}$ motor neurons compared to Gars$^{+/+}$. 1978 genes are upregulated (log FC>1.5; p value<0.05) and 126 are downregulated (log FC<-1.5; p value<0.05). Analysis was performed on 5-6 animals per genotype at 8 weeks of age.

We next compared ribosome-associated mRNA immunoprecipitated from Gars motor neurons to that from Gars$^{C201R/+}$ or Gars$^{P278KY/+}$ motor neurons at 8 weeks of age, the same age at which we performed FUNCAT. Compared to Gars$^{+/+}$, Gars$^{C201R/+}$ motor neurons showed 1,978 upregulated and 126 downregulated transcripts with an absolute log FC of 1.5 or greater and a FDR and p value of less than 0.05 (FIG. 2C). Gars$^{P278KY/+}$ motor neurons contained 633 upregulated and 237 downregulated transcripts that also met these requirements (FIG. 2D). The top upregulated transcripts in Gars$^{C201R/+}$ and Gars$^{P278KY/+}$ motor neurons represent a distinct and reproducible disease signature, as none are in common with the top upregulated transcripts following sciatic nerve crush, but over half are shared between the two mutant Gars alleles (FIG. 2E). We also performed RiboTagging in 2 week-old, pre-disease onset Gars$^{C201R/+}$ motor neurons, and confirmed early upregulation of six of the top upregulated transcripts identified at 8 weeks (data not shown). Thus, before neuropathy is detectable, gene expression changes are already taking place.

To determine if the translational changes seen in mutant Gars motor neurons are also occurring at the transcriptional level, we performed whole spinal cord RNA sequencing on 8 week old Gars$^{C201R/+}$ and Gars$^{P278KY/+}$ mice, as well as the additional Gars$^{delETAQ/+}$ model. We observed a striking similarity among the top 10 upregulated transcripts from both RiboTagging and RNA sequencing experiments, and among all three mouse models (FIG. 2E). These data suggest that gene expression changes are present at both translational and transcriptional levels, and that the same disease mechanism is likely occurring with all three mutations in Gars, including the human mutation, delETAQ.

Figure 3A:
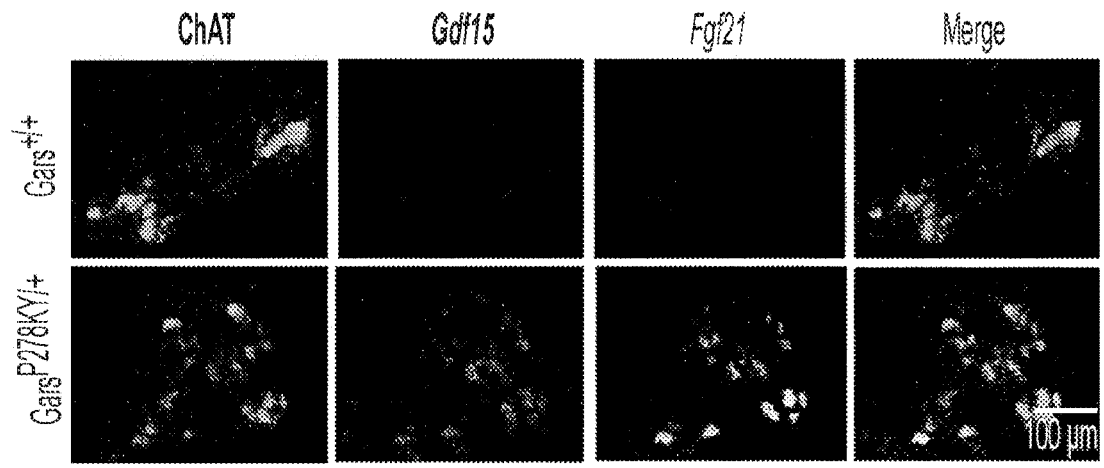
FIG. 3A shows representative images of RNAscope in situ hybridization using probes for 5 of the upregulated transcripts identified from Ribotagging and RNA sequencing experiments. Gars$^{+/+}$ motor neurons are labeled with ChAT but show no expression of disease-related transcripts, Gdf15 or Fgf21. Gars$^{P278KY/+}$ motor neurons labeled with ChAT show robust upregulation of Gdf15 and Fgf21 in a subset of motor neurons. Some ChAT-labelled motor neurons do not show expression of disease-related transcripts.
Figure 3B:
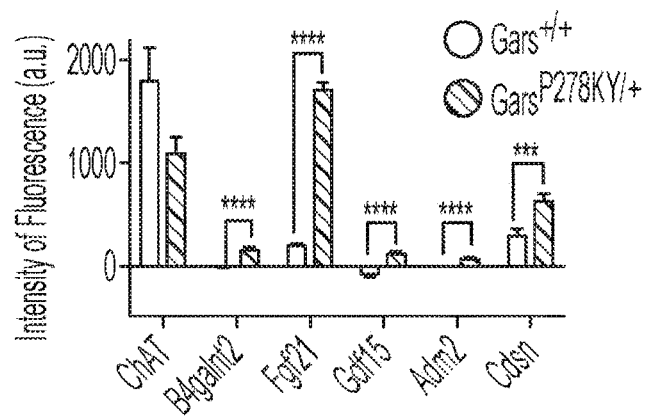
FIG. 3B shows the quantification of fluorescence in Gars$^{+/+}$ and Gars$^{P278KY/+}$ motor neurons.

Example 3. Alpha Motor Neurons are the Only Cell Type to Express Disease Signature within the Spinal Cord To validate our gene expression data, as well as to address questions of cell type-specificity within the spinal cord, we used RNAscope in situ hybridization. All motor neurons were labelled with ChAT and probed for expression of five of the top upregulated transcripts from RiboTagging and RNA sequencing data that were in common among multiple Gars models. These transcripts were fibroblast growth factor 21 (Fgf21), growth differentiation factor 15 (Gdf15), adrenomedullin 2 (Adm2), corneodesmosin (Cdsn), and Beta-1,4-N-Acetyl-Galactosaminyltransferase 2 (B4galnt2). No or very little expression of the five transcripts were seen in any cell types within Gars$^{+/+}$ spinal cord (FIGS. 3A-3B). In contrast, robust upregulation of all five transcripts was confirmed in Gars$^{P278KY/+}$ motor neurons, but in no other cell type of the spinal cord (FIGS. 3A-3B). Fgf21 is a metabolic regulator most highly expressed by the liver, but also expressed from skeletal muscle and central nervous system neurons upon mitochondrial dysfunction (Fisher and Maratos-Flier 2016). Together with Fgf21, Gdf15 is also known to signal mitochondrial dysfunction, but neither has ever been shown to be expressed from motor neurons. We also show Cdsn expression from motor neurons for the first time. Cdsn is a component of tight junctions in the skin, but is also highly upregulated in Gars$^{P278KY/+}$ motor neurons.

Figure 3C:
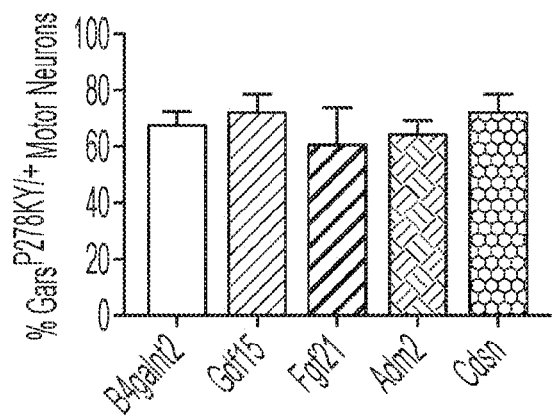
FIG. 3C shows that approximately 70% of Gars$^{P278KY/+}$ motor neurons expressed the 5 disease-associated transcripts.
Figure 3D:
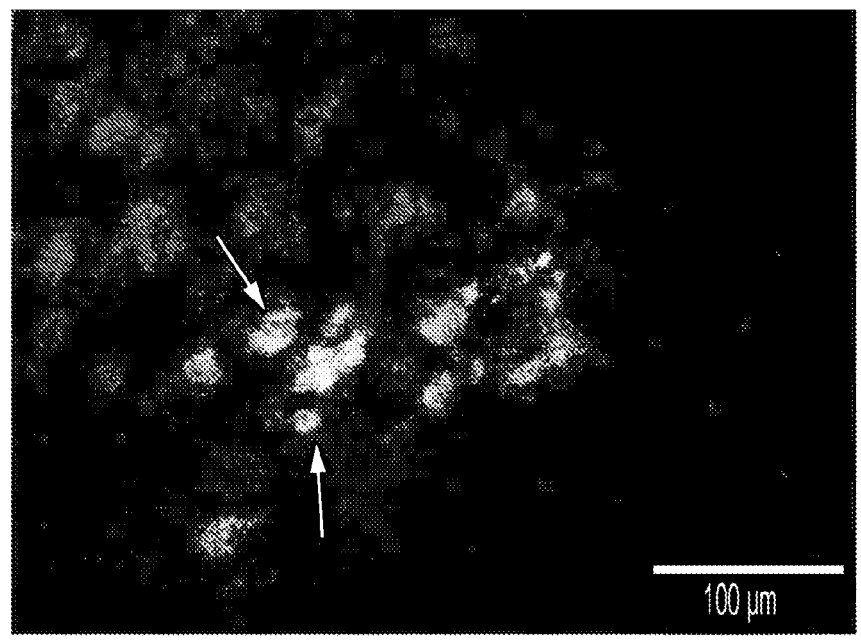
FIG. 3D shows that all Gars$^{P278KY/+}$ motor neurons labeled with ChAT that did not express Fgf21 were labeled with the gamma motor neuron marker, Err3 (arrows).
Figure 3E:
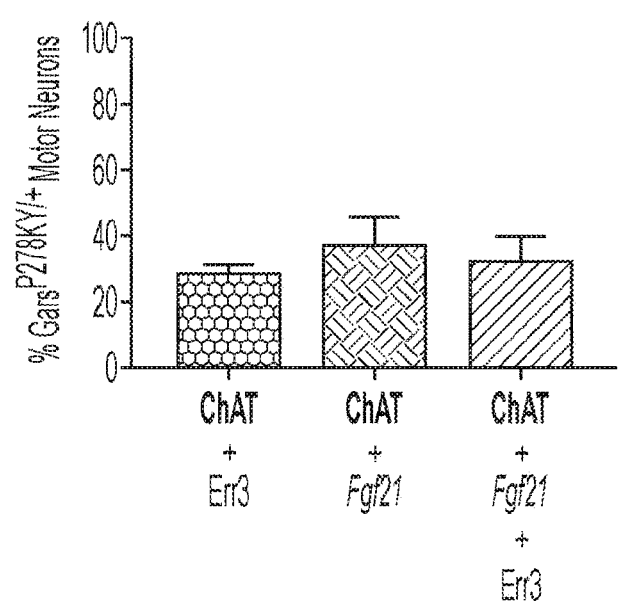
FIG. 3E shows the quantification of expression in FIG. 3D. Note that some Err3 labeled motor neurons do express Fgf21, probably indicating that Err3 is also expressed in some alpha motor neurons. Analysis was performed using 4 animals per genotype at 8 weeks of age. Values in FIG. 3B are the sum of fluorescence intensity in all 4 animals per genotype±SD. Values in FIGS. 3C and 3E are mean±SD. *=p<0.001, **=p<0.0001.

Interestingly, only about 70% of Gars$^{P278KY/+}$ motor neurons express the disease signature (FIG. 3C). Spinal cord motor neurons can be divided into gamma and alpha populations. Gamma motor neurons are smaller, provide sensitivity to muscle stretch, and comprise about 30% of the total population. Alpha motor neurons are larger, provide muscle force, and make up the resulting 70% (Stifani 2014). Because approximately 70% of mutant Gars motor neurons express the disease signature and because in Gars$^{P278KY/+}$ mice the largest motor axons are preferentially lost, we hypothesized that alpha motor neurons were the population showing these gene expression changes and that gamma motor neurons were correspondingly resistant (Sebum et al. 2006). To test this hypothesis we labeled all motor neurons with ChAT, used Fgf21 as our marker of the disease signature, and labeled gamma motor neurons with Err3 (Friese et al. 2009). In every case where a ChAT-positive motor neuron showed no expression of Fgf21 (28.9%±4.6) of the total motor neuron population), it was clearly labeled with Err3, indicating that gamma motor neurons are resistant to expressing the disease signature and that alpha motor neurons are the population most susceptible (FIGS. 3D-3E).

Figure 4A:
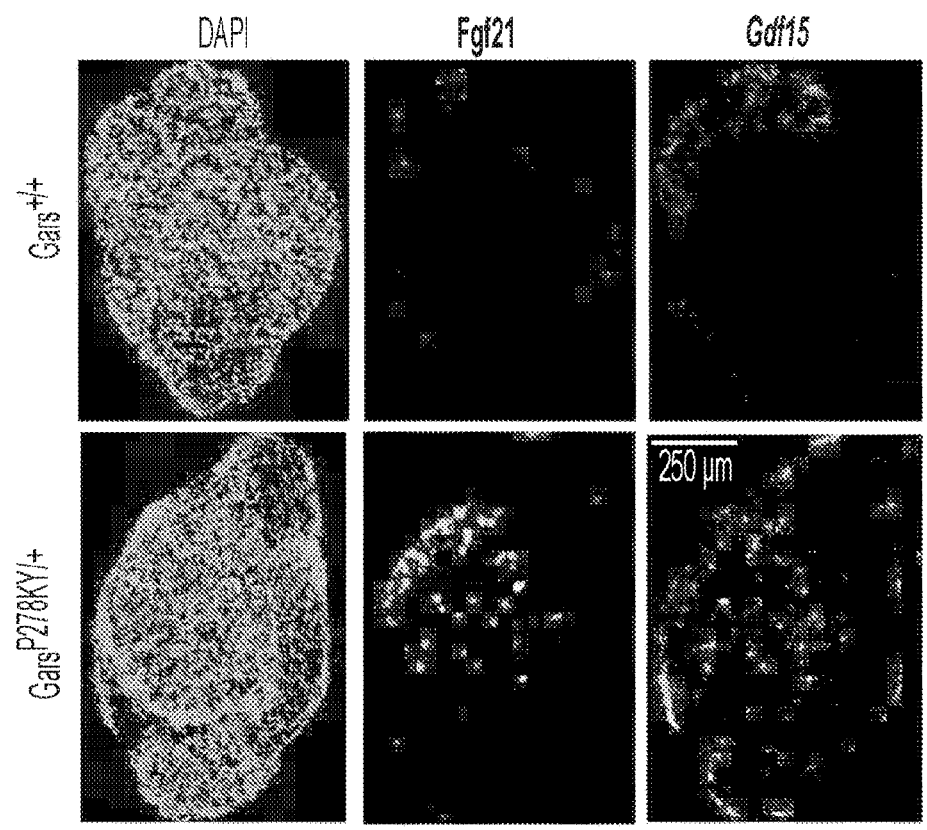
FIG. 4A shows that there was no expression of disease-associated transcripts in Gars$^{+/+}$ dorsal root ganglia but there was expression of Fgf21 and Gdf15 in a subset of Gars$^{P278KY/+}$ dorsal root ganglia.
Figure 4B:
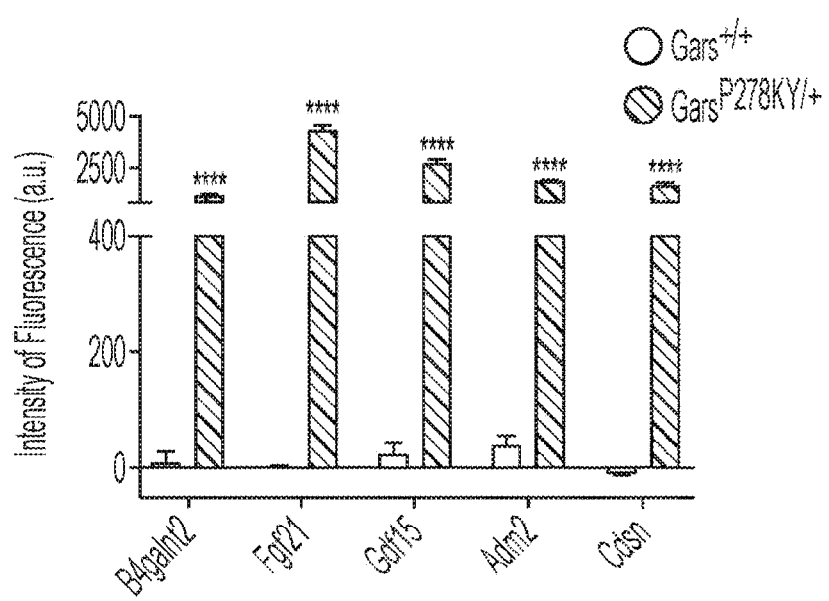
FIG. 4B shows that all five transcripts upregulated in Gars$^{P278KY/+}$ motor neurons are also upregulated in sensory neurons and the quantification of FIGS. 4A and 4B.

Because Gars$^{P278KY/+}$ mice experience sensory axon degeneration we wondered if the same disease mechanism could be occurring in this neuronal population as in motor neurons. We reasoned that if this was true, sensory neurons would express a similar gene expression signature to motor neurons. To test this we probed for the same five disease-associated transcripts in dorsal root ganglia as in the spinal cord. Again, all five transcripts showed no expression in Gars$^{+/+}$ sensory neurons, but a robust upregulation only in a subset of Gars$^{P278KY/+}$ sensory neurons (FIGS. 4A-4B).

Figure 4C:
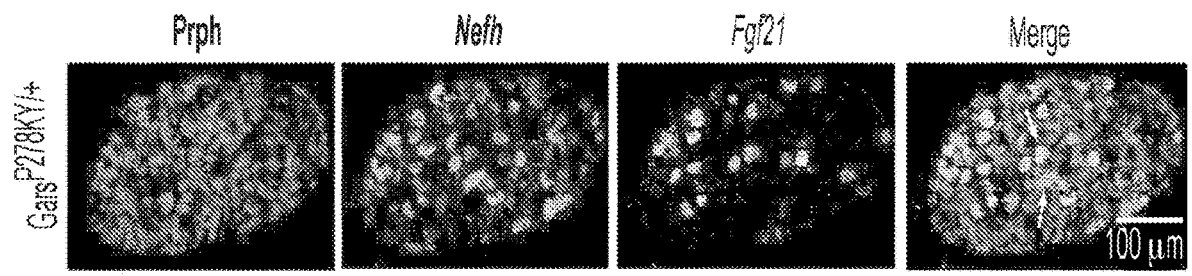
FIG. 4C shows Peripherin (Prph) labels on small fiber sensory neurons and Neurofilament-heavy chain (Nefh) labels on medium-large fiber neurons. Fgf21 expression is only seen in Nefh-expressing neurons, although not in all.
Figure 4D:
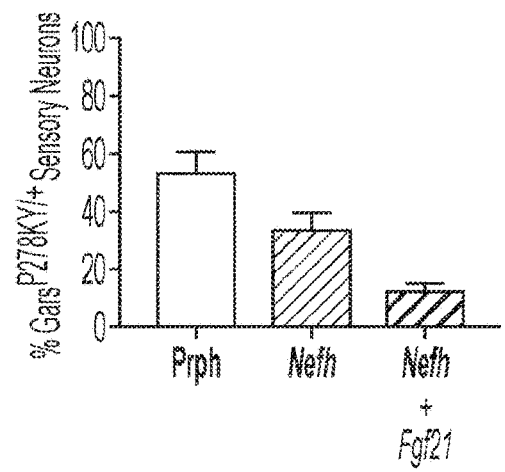
FIG. 4D shows the quantification of expression in FIG. 4C.
Figure 4E:
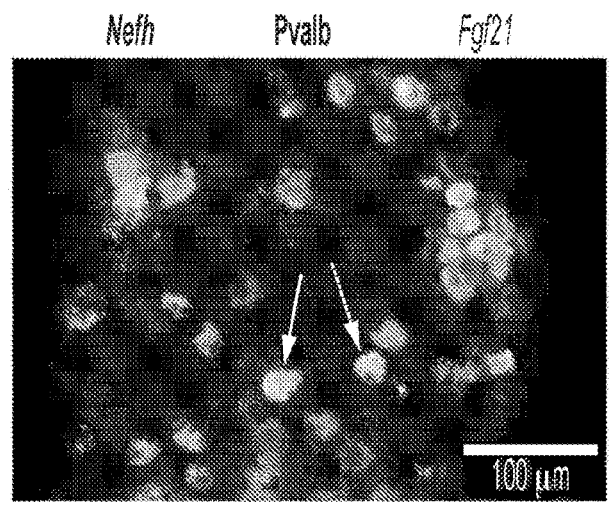
FIG. 4E shows mechanosensitive sensory neurons that are labeled solely with Nefh, while the proprioceptive neurons are labeled with Nefh and parvalbumin (Pvalb). Fgf21 expression is seen in mechanosensitive and proprioceptive sensory neurons.
Figure 4F:
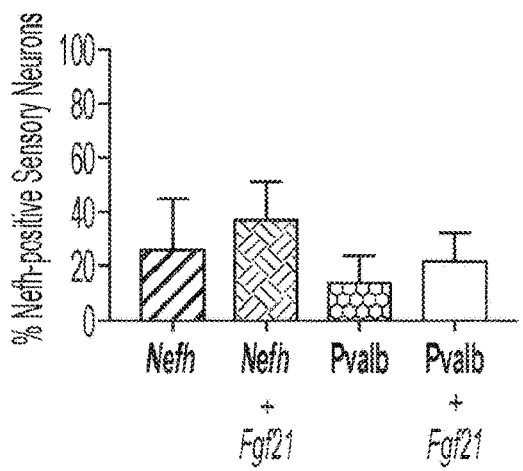
FIG. 4F shows the quantification of expression in FIG. 4E. Analysis used 4 animals per genotype at 8 weeks of age. Values in B are the sum of fluorescence in all 4 animals per genotype±SD. Values in FIGS. 4D and 4F are mean±SD. ****=p<0.0001.

In light of our findings in the spinal cord, we tested if expression of the disease signature was associated with neuronal size. Small fiber sensory neurons were labeled with peripherin (Prph), medium-large fiber sensory neurons were labeled with neurofilament heavy chain (Nefh), and Ffg21 was used as the disease marker (Ferri et al. 1990). Only Nefh-positive sensory neurons express Fgf21, indicating that larger sensory neurons are more susceptible to these disease-associated gene expression changes and smaller sensory neurons are resistant (FIGS. 4C-4D). Because not all Nefh-positive sensory neurons showed expression of Fgf21, we next tested if there was any functional correlation. Mechanosensitive and proprioceptive sensory neurons both express Nefh, but proprioceptive neurons can be distinguished by the additional expression of parvalbumin (Pvalb) (Le Pichon and Chesler 2014). In Gars$^{P278KY/+}$ dorsal root ganglia, both mechanosensitive and proprioceptive sensory neurons express Fgf21 (FIGS. 4E-4F). Thus, as in the spinal cord, within the dorsal root ganglion, expression of the disease signature is exclusive to sensory neurons and correlates with neuron size.

Figure 5A:
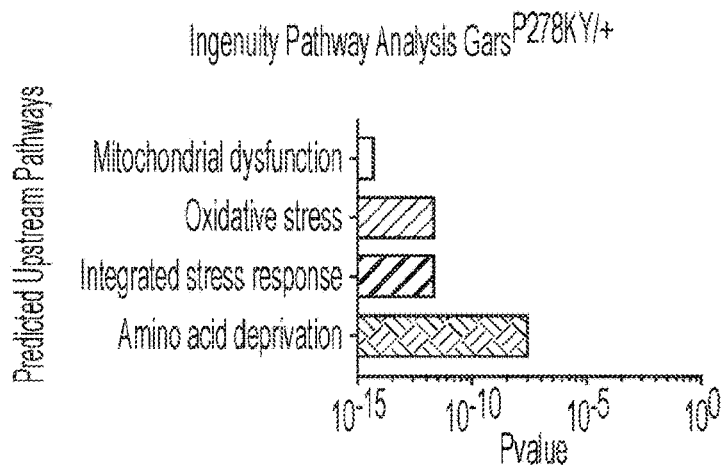
FIG. 5A shows the Ingenuity Pathway Analysis of upregulated ribosome-associated mRNA with log FC 1.5 and FDR<0.05 in Gars$^{P278KY/+}$ motor neurons.

Example 4. The Integrated Stress Response is Activated Through GCN2 Kinase in Mutant Gars Motor Neurons To obtain a more global perspective of the mutant Gars gene expression signature, we performed Ingenuity Pathway Analysis (IPA) using upregulated genes with a log FC of 1.5 or greater and a p value of 0.05 or less from the Gars$^{P278KY/+}$ RiboTagging dataset. Among the top predicted upstream pathways was the integrated stress response (ISR) (FIG. 5A). The ISR is a highly conserved cell stress pathway found in all eukaryotic cells that can be triggered by a variety of intrinsic and extrinsic cell stressors, each through a distinct protein kinase. PERK is activated by ER stress, GCN2 by amino acid deprivation, PKR by viral infection, and HRI by heme deprivation (Pakos-Zebrucka et al. 2016). Activation of any one of these four kinases results in phosphorylation of the translation initiation factor, eIF2α, a subsequent reduction in cap-dependent mRNA translation, and upregulation of specific stress response genes through the transcription factor ATF4. We determined that many of the top upregulated transcripts in mutant Gars motor and sensory neurons are direct targets of ATF4, including Fgf21, Gdf15, Cdsn, Adm2, and B4galnt2, among others. Thus, the ISR is activated in mutant Gars motor and sensory neurons, and we next wanted to test which kinase was responsible for its activation.

Figure 5B:
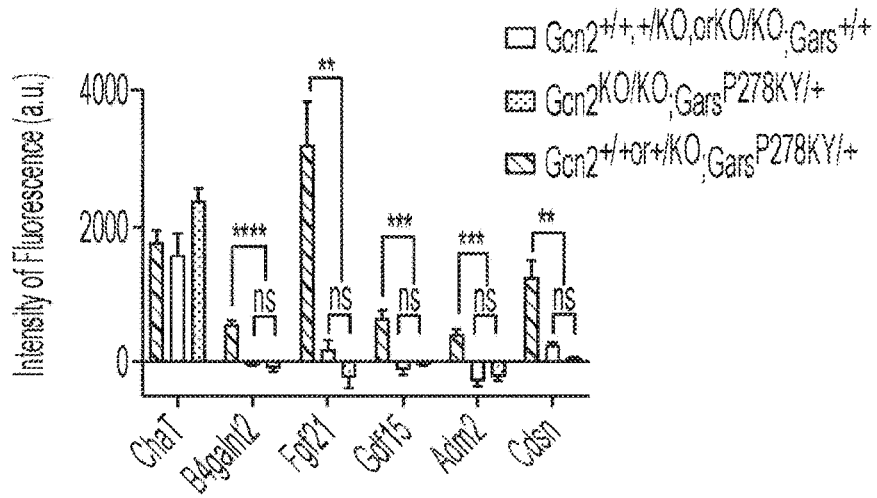
FIG. 5B shows that the genetic removal of GCN2 kinase from Gars$^{P278KY/+}$ mice shuts off expression of ATF4 target genes in motor neurons.
Figure 5C:
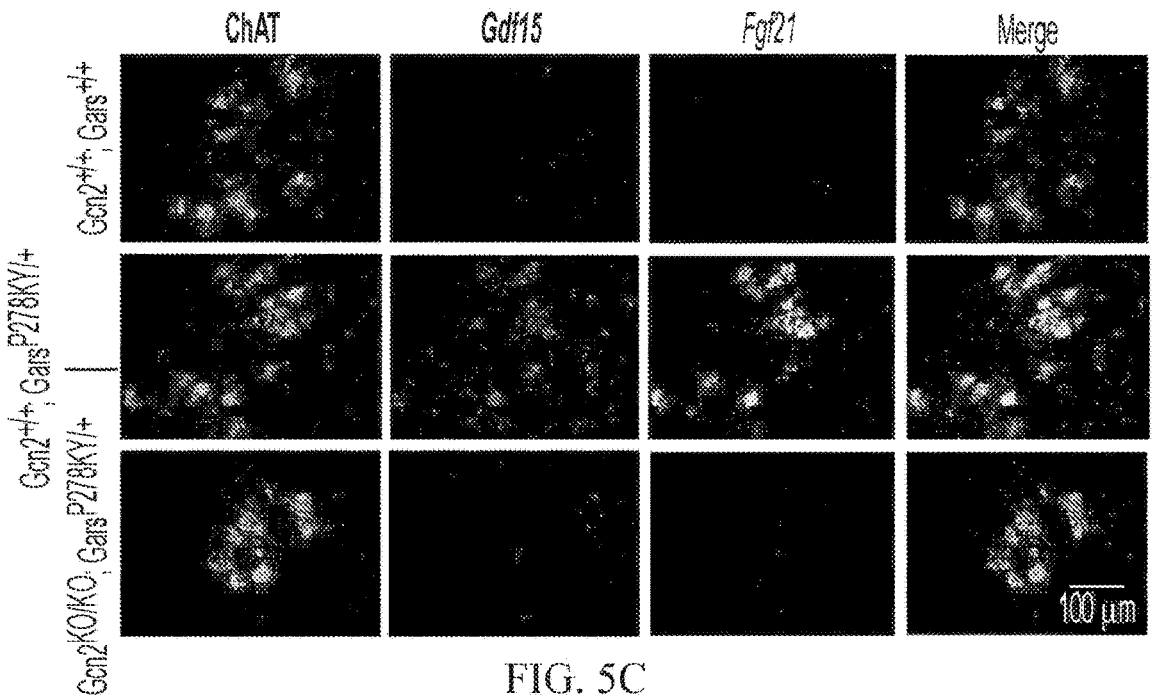
FIG. 5C shows that Gcn2$^{+/+}$; Gars$^{+/+}$ motor neurons show no expression of ATF4 target genes, while Gcn2$^{+/+}$; Gars$^{P278KY/+}$ motor neurons show robust upregulation. Gcn2$^{KO/KO}$; Gars$^{P278KY/+}$ motor neurons show no expression of ATF4 target genes. Analysis performed with 3 animals per genotype at 8 weeks of age. Values in FIG. 5B are mean±SD. , p<0.01; *, p<0.001; ****=p<0.0001.

Because the IPA also suggested amino acid deprivation as a predicted upstream pathway, we hypothesized that the ISR was being activated by GCN2 kinase. We tested this genetically by crossing GCN2 knockout mice (Gcn2$^{KO/KO}$) with Gars$^{P278KY/+}$ mice. We again probed for expression of the same five ATF4 target genes in the spinal cords of 8 week old mice. Gars mice with GCN2 (Gcn2$^{+/+}$; Gars$^{+/+}$) showed no expression of ATF4 target genes and Gars$^{P278KY/+}$ mice with GCN2 (Gcn2$^{+/+}$; Gars$^{P278KY/+}$) showed robust upregulation in motor neurons (FIGS. 5B-5C). Genetic removal of GCN2 from Gars$^{P278KY/+}$ mice (Gcn2$^{KO/KO}$; Gars$^{P278KY/+}$) completely shut off expression of all five ATF4 target genes in motor neurons (FIGS. 5B-5C). This was confirmed with whole spinal cord RNA sequencing, which revealed that upon removal of GCN2 there are only 9 differentially expressed protein coding genes with established names between Gars$^{+/+}$ and Gars$^{P278KY/+}$ mice (Gcn2$^{KO/KO}$; Gars$^{+/+}$ vs Gcn2$^{KO/KO}$; Gars$^{P278KY/+}$) (Table 1).

TABLE 1

Differentially Expressed Genes in Gcn2$^{KO/KO}$; Gars$^{P278KY/+}$ spinal cord versus Gcn2$^{KO/KO}$; Gars$^{+/+}$: There are only 7 upregulated and 6 downregulated established protein coding genes inGcn2$^{KO/KO}$; Gars$^{P278KY/+}$ spinal cord compared to Gcn2$^{KO/KO}$; Gars$^{+/+}$. Analysis performed using 3-5 mice per genotype.

| Gene Name | LogFC | P Value | FDR |
|---|---|---|---|
| Rps2 | 13.4320471 | 1.51E−112 | 2.29E−108 |
| Ncoa4-ps | 11.57369861 | 2.72E−76 | 1.38E−72 |
| Hmga1 | 11.476878 | 1.77E−74 | 6.72E−71 |
| Glo1-ps | 11.01104267 | 7.74E−66 | 2.35E−62 |
| Rpl34 | 10.96327615 | 5.83E−65 | 1.47E−61 |
| Rnps1-ps | 10.52922891 | 3.23E−57 | 5.44E−54 |
| Rps7-ps3 | 10.45685658 | 5.25E−56 | 7.24E−53 |
| Rpl28 | 10.02462176 | 1.27E−48 | 1.13E−45 |
| Rps18-ps | 9.881925935 | 2.82E−46 | 2.37E−43 |
| Ldhb-ps | 9.826394064 | 2.21E−45 | 1.76E−42 |
| Srsf3-ps | 9.69823495 | 2.49E−43 | 1.80E−40 |
| Rpl15-ps6 | 9.212083264 | 4.96E−36 | 2.69E−33 |
| Rpl27a-ps | 9.184365003 | 1.42E−35 | 7.44E−33 |
| Rps12 | 8.859592333 | 4.24E−31 | 2.07E−28 |
| Tmem41b-ps | 8.452467925 | 5.16E−53 | 5.21E−50 |
| Gpi-ps | 8.27100681 | 9.51E−63 | 1.80E−59 |
| Mrpl48 | 8.006921589 | 2.87E−22 | 1.14E−19 |
| Rps18 | 7.977730073 | 5.61E−22 | 2.18E−19 |
| Lamtor3-ps | 7.965541291 | 7.03E−22 | 2.66E−19 |
| Rps18 | 7.923015822 | 1.92E−55 | 2.24E−52 |
| Rtraf-ps | 7.766924484 | 6.46E−42 | 4.26E−39 |
| Psma5-ps | 6.838230394 | 1.18E−29 | 5.41E−27 |
| Rpl15 | 6.172886891 | 8.74E−22 | 3.23E−19 |
| Rpl10a-ps4 | 6.126378683 | 3.92E−21 | 1.38E−18 |
| Rps19 | 6.06304125 | 1.41E−56 | 2.14E−53 |
| Ubb-ps | 6.020385642 | 6.79E−79 | 5.15E−75 |
| Atp5pb-ps | 5.782145061 | 9.51E−18 | 2.88E−15 |
| Ftl1-ps1 | 5.654728334 | 5.25E−63 | 1.14E−59 |
| Lypd3 | 5.58506499 | 1.22E−21 | 4.39E−19 |
| Rps13 | 5.443421282 | 8.59E−56 | 1.09E−52 |
| Akt2 | 4.972813612 | 1.89E−20 | 6.35E−18 |
| Atg4a | 4.780984448 | 1.76E−18 | 5.56E−16 |
| Psenen-ps | 4.42649374 | 2.21E−35 | 1.11E−32 |
| Capza1 | 4.162132747 | 7.71E−44 | 5.84E−41 |
| Amd | 3.795407541 | 9.79E−39 | 5.71E−36 |
| Amd2 | 3.788876628 | 1.11E−40 | 6.98E−38 |
| Rps2 | 3.365991516 | 1.35E−24 | 5.70E−22 |
| Lad1 | 2.933061146 | 9.61E−14 | 2.47E−11 |
| Erdr1 | 2.653375072 | 2.79E−18 | 8.64E−16 |
| Nova2os | 2.579812779 | 1.71E−09 | 3.17E−07 |
| Fb1-ps2 | 2.562883158 | 1.56E−10 | 3.14E−08 |
| Ect2l | 2.463671052 | 3.41E−11 | 7.61E−09 |
| Tnni1 | 2.396810566 | 2.45E−14 | 6.40E−12 |
| A430106G13Rik | 2.352000899 | 1.28E−10 | 2.63E−08 |
| Mrpl27-ps | 2.193610117 | 2.32E−07 | 3.23E−05 |
| Gapdh-ps | 2.003645602 | 2.10E−07 | 2.95E−05 |
| Rps8-ps5 | 1.965842501 | 1.66E−07 | 2.38E−05 |
| Eef1a1-ps | 1.946951952 | 3.20E−05 | 0.00327195 |
| Cox7c-ps | 1.911725803 | 7.14E−13 | 1.75E−10 |
| Taf9-9 | 1.78936859 | 1.56E−11 | 3.58E−09 |
| Nfyc-ps | 1.720823495 | 5.38E−08 | 8.41E−06 |
| Myh3 | 1.678577737 | 6.69E−06 | 0.00075657 |
| C4a | 1.613505494 | 8.63E−10 | 1.70E−07 |
| Actb-ps1 | 1.593366508 | 0.00024378 | 0.01931 |
| BC002163 | 1.58184294 | 8.24E−11 | 1.76E−08 |
| Ap2m1-ps | 1.575766825 | 1.13E−10 | 2.35E−08 |
| Hdac1-ps | 1.566870596 | 4.57E−09 | 8.14E−07 |
| Tmsb15b2 | 1.549206632 | 6.90E−09 | 1.18E−06 |
| Zfp783 | −1.547338851 | 4.44E−11 | 9.61E−09 |

TABLE 1-continued

Differentially Expressed Genes in Gcn2$^{KO/KO}$; Gars$^{P278KY/+}$ spinal cord versus Gcn2$^{KO/KO}$; Gars$^{+/+}$: There are only 7 upregulated and 6 downregulated established protein coding genes inGcn2$^{KO/KO}$; Gars$^{P278KY/+}$ spinal cord compared to Gcn2$^{KO/KO}$; Gars$^{+/+}$.
Analysis performed using 3-5 mice per genotype.

| Gene Name | LogFC | P Value | FDR |
|---|---|---|---|
| Ctdsp2-ps | −1.562856813 | 2.49E−08 | 4.11E−06 |
| Ccl21d | −1.566776424 | 5.29E−06 | 0.00061641 |
| Mif-ps | −1.574149736 | 9.03E−08 | 1.37E−05 |
| Eif4a3l2 | −1.626636408 | 4.22E−07 | 5.61E−05 |
| Rps15 | −1.654412348 | 4.23E−12 | 1.00E−09 |
| Sox4os1 | −1.700085698 | 1.03E−09 | 2.00E−07 |
| Tdg-ps | −1.716393171 | 2.93E−07 | 4.01E−05 |
| Ndufa12-ps | −1.749354164 | 4.80E−12 | 1.12E−09 |
| Cox5b-ps | −1.840052084 | 2.21E−15 | 6.09E−13 |
| Eef2-ps | −1.84619464 | 6.94E−13 | 1.72E−10 |
| Cd55os | −1.855671794 | 3.61E−08 | 5.76E−06 |
| Tdg | −1.877071742 | 1.91E−15 | 5.36E−13 |
| Slc10a4l | −1.887604137 | 6.43E−09 | 1.12E−06 |
| Hadhb-ps | −1.939670489 | 5.47E−17 | 1.63E−14 |
| Calca | −2.019063947 | 7.15E−19 | 2.30E−16 |
| Commd1b | −2.049550745 | 6.90E−16 | 1.97E−13 |
| Zfp968-ps | −2.184534689 | 4.01E−19 | 1.32E−16 |
| Tspan10 | −2.428282143 | 2.13E−25 | 9.23E−23 |
| Rpl7-ps | −2.551796784 | 1.35E−14 | 3.60E−12 |
| Dnajb6-ps | −2.582154391 | 1.25E−23 | 5.11E−21 |
| Actr3-ps | −2.632627399 | 1.50E−28 | 6.68E−26 |
| Galnt2l | −2.96284136 | 2.95E−36 | 1.66E−33 |
| Glns | −3.496093681 | 9.90E−40 | 6.00E−37 |
| Rpl7-ps9 | −3.609521114 | 6.68E−21 | 2.30E−18 |
| Rbpsuh | −3.663860505 | 5.68E−30 | 2.69E−27 |
| Csnk2a3 | −4.035419929 | 1.07E−54 | 1.16E−51 |

Example 5. Genetic Removal of GCN2 Kinase Alleviates Gars Neuropathy

Whether activation of the ISR is helpful or harmful to cells is highly dependent upon cell type, disease context, and the length of activation of the response. For example, genetic removal of GCN2 kinase and subsequent shutdown of the ISR in a mouse model of rapid cerebellar ataxia exacerbates neurodegeneration (Ishimura et al. 2016). In contrast, genetic removal of GCN2 or PERK from APP/PS1 Alzheimer's disease mice prevents impairments in spatial memory and synaptic plasticity, indicating that long-lasting imbalances in translation contribute to chronic neurodegenerative diseases (Ma et al. 2013).

Figure 6A:
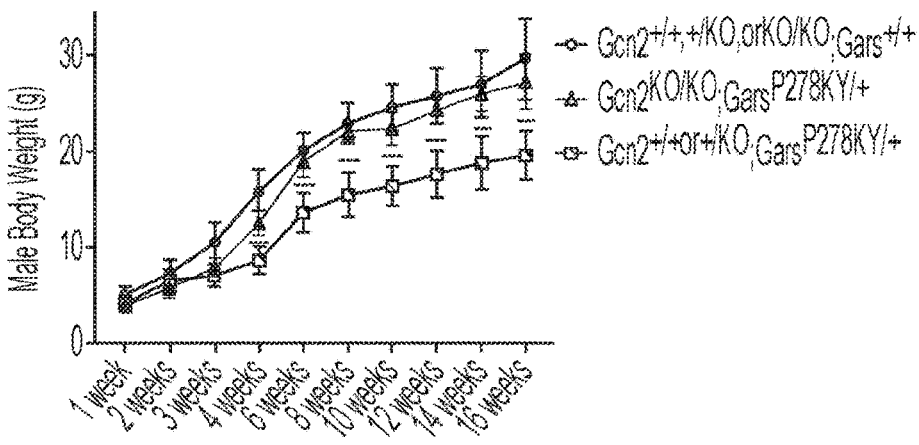
FIG. 6A shows that the body weight of male Gcn2$^{KO/KO}$; Gars$^{P278KY/+}$ mice is significantly increased over Gcn2$^{+/+}$ $^{or}$ $^{+/-}$; Gars$^{P278KY/+}$.
Figure 6B:
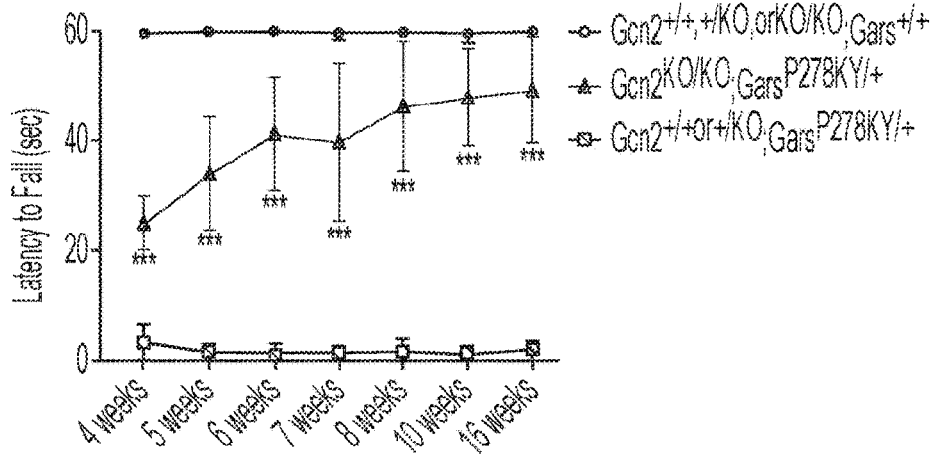
FIG. 6B shows that Gcn2$^{KO/KO}$; GarsP2$^{P278KY/+}$ mice have improved motor function as measured by the wire hang test. Mice are place on an inverted grid and latency to fall is timed. The test is stopped after 60 seconds and the mean of 3 trials is reported for each day. Analysis performed with 18-22 mice per grouped genotype.
Figure 6C:
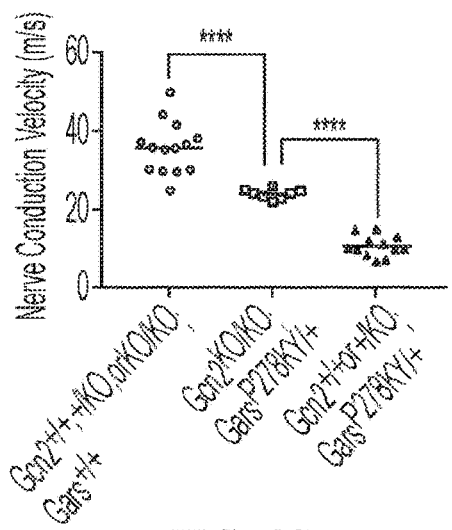
FIG. 6C shows that Gcn2$^{KO/KO}$; Gars$^{P278KY/+}$ mice have increased nerve conduction velocity of the sciatic nerve (23.9 m/s±1.3) compared to Gcn2$^{+/+}$ $^{or}$ $^{+/KO}$; Gars$^{P278KY/+}$ (10.7 m/s±2.7), although not completely restored to Gcn2$^{+/+,\ +/KO\ or\ KO/KO}$; Gars$^{+/+}$ (35.7 m/s±6.6). Analysis performed with 8-14 mice per grouped genotype.

We found that homozygous genetic removal of GCN2 kinase significantly improves CMT2D neuropathy in mice. Both male (FIG. 6A) and female (not shown) Gcn2$^{KO/KO}$; Gars$^{P278KY/+}$ mice have body weights nearly restored to Gars levels. Motor performance of mice is improved as measured by the wire hang test. Gars mice with or without GCN2 (Gcn2$^{+/+, +/KO, or KO/KO}$; Gars$^{+/+}$) can hang on to an inverted wire grid for the duration of the test, 60 seconds, while Gars$^{P278KY/+}$ mice with GCN2 (Gcn2$^{+/+ or +/KO}$; Gars$^{P278KY/+}$) struggle to hang on for even a few seconds. Gcn2$^{KO/KO}$; Gars$^{P278KY/+}$ mice have an increased latency to fall that approaches that of Gcn2$^{+/+, +/KO, or KO/KO}$; Gars$^{+/+}$ mice by 16 weeks of age (FIG. 6B). Gcn2$^{KO/KO}$; Gars$^{P278KY/+}$ mice also have improved peripheral nerve function. At 8 weeks of age Gcn2$^{+/+, +/KO, or KO/KO}$; Gars$^{+/+}$ mice have an average sciatic nerve conduction velocity of 35.7 m/s±6.6, Gcn2$^{+/+ or +/KO}$; Gars$^{P278KY/+}$ have an average of 10.7 m/s±2.7, and Gcn2$^{KO/KO}$; Gars$^{P278KY/+}$ mice have an average of 23.9 m/s±1.3 (FIG. 6C). Improvements in conduction velocity persist through at least 16 weeks of age. At 16 weeks of age there is no longer a statistical difference between Gcn2$^{+/+, +/KO, or KO/KO}$; Gars$^{+/+}$ mice and Gcn2$^{KO/KO}$; Gars$^{P278KY/+}$ mice, as almost all Gcn2$^{KO/KO}$; Gars$^{P278KY/+}$ mice have conduction velocities well within the Gcn2$^{+/+, +/KO, or KO/KO}$; Gars$^{+/+}$ range (data not shown).

Figure 6D:
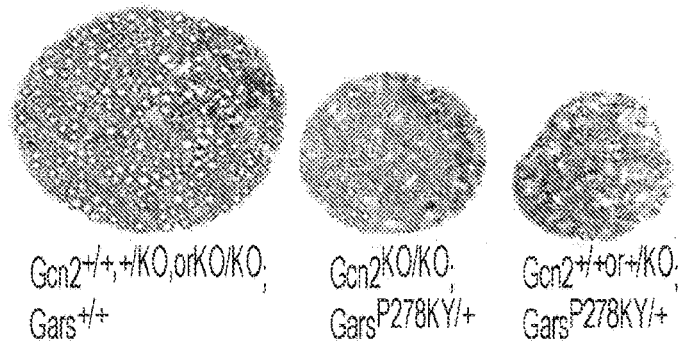
FIG. 6D shows that the motor branch of the femoral nerve in Gcn2$^{KO/KO}$; Gars$^{P278KY/+}$ mice is intermediate in size compared to Gcn2$^{+/+,\ +/KO,\ or\ KO/KO}$, Gars$^{+/+}$ and Gcn2$^{+/+\ or\ +/-}$, Gars$^{P278KY/+}$.
Figure 6E:
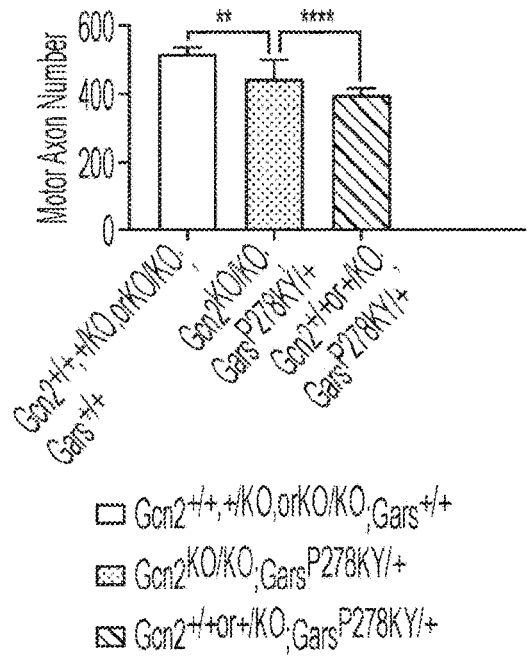
FIG. 6E shows that motor axon loss in the femoral nerve is partially rescued in Gcn2$^{KO/KO}$; Gars$^{P278KY/+}$ mice. Gcn2$^{KO/KO}$; Gars$^{P278KY/+}$ mice have an average of 448±55 motor axons, compared to 523±15 in Gcn2$^{+/+,\ +/KO,\ or\ KO/KO}$; Gars$^{+/+}$ mice and 398±23 in Gcn2$^{+/+\ or\ +/KO}$; Gars$^{P278KY/+}$ mice. Analysis performed with 13-14 mice per grouped genotype.
Figure 6F:
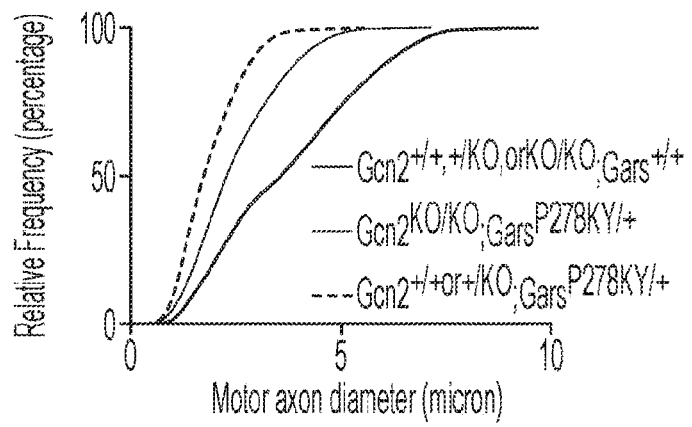
FIG. 6F shows the diameter measurement of all motor axons in the femoral nerve. There is a higher frequency of smaller diameter axons in Gcn2$^{+/+\ or\ +/KO}$; Gars$^{P278KY/+}$ mice compared to Gcn2$^{+/+,\ +/KO,\ or\ KO/KO}$; Gars$^{+/+}$, which is partially corrected in Gcn2$^{KO/KO}$; Gars$^{P278KY/+}$ mice. Analysis performed with at least 6 mice per grouped genotype.

A degree of motor axon loss was also prevented by removing GCN2 from Gars$^{P278KY/+}$ mice. The motor branch of the femoral nerve contained more axons in Gcn2$^{KO/KO}$; Gars$^{P278KY/+}$ mice (448±55) than in Gcn2$^{+/+, +/KO or KO/KO}$; Gars$^{P278KY/+}$ mice (398±23) at 8 weeks of age (FIGS. 6D-6E), and by 16 weeks of age there was no longer a statistical difference between Gcn2$^{KO/KO}$; Gars$^{P278KY/+}$ and Gcn2$^{+/+, +/KO, or KO/KO}$; Gars$^{+/+}$ (data not shown). Reduction in motor axon diameter was also partially rescued by removal of GCN2 at 8 weeks of age, and this effect persisted through at least 16 weeks of age (FIG. 6F).

Figure 6G:
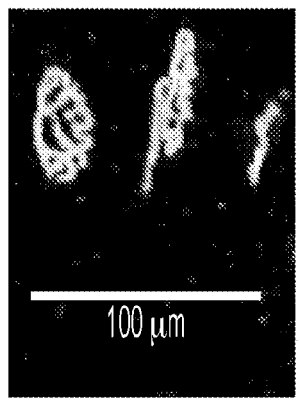
FIG. 6G shows examples of fully innervated neuromuscular junctions (NMJs) in the gastrocnemius muscle of Gcn2$^{+/+,\ +/KO,\ or\ KO/KO}$; Gars$^{+/+}$ mice. The nerve terminal fully covers the post-synaptic acetylcholine receptors.
Figure 6H:
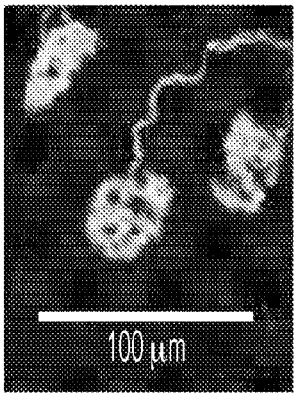
FIG. 6H shows an example of two partially innervated NMJs in Gcn2$^{+/+\ or\ +/KO}$; Gars$^{P278KY/+}$ mice. There are several regions of the post-synapse not covered by nerve. The arrow shows an example of a fully innervated, but morphologically abnormal, NMJ. Most fully innervated NMJs in Gcn2$^{+/+\ or\ +/KO}$; Gars$^{P278KY/+}$ mice do not show the classic "pretzel" shape.
Figure 6I:
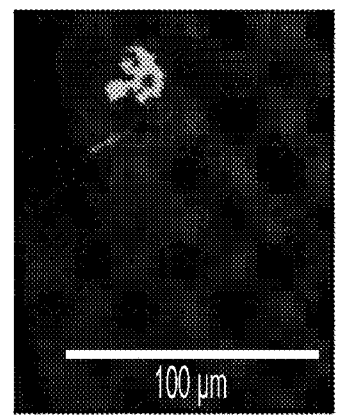
FIG. 6I shows an example of a completely denervated NMJ in Gcn2$^{+/+\ or\ +/KO}$; Gars$^{P278KY/+}$ mice, where the post-synapse has no contact with the nerve.
Figure 6J:
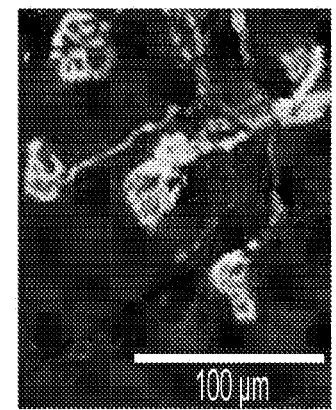
FIG. 6J shows fully innervated NMJs in Gcn2$^{KO/KO}$; Gars$^{P278KY/+}$ mice. Most fully innervated NMJs look morphologically normal with the classic "pretzel" shape.
Figure 6K:
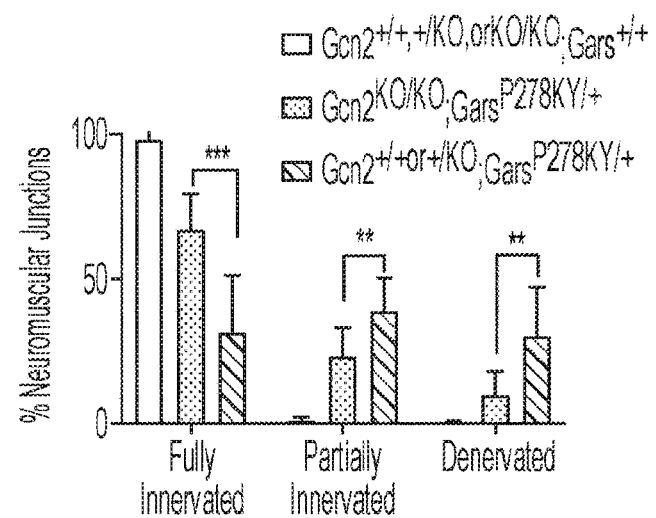
FIG. 6K shows the quantification of fully innervated, partially innervated, and denervated NMJs by genotype. In Gcn2$^{+/+,\ +/KO,\ or\ KO/KO}$; Gars$^{+/+}$ mice the vast majority of NMJS are fully innervated (98.2%±2.1), with a very small minority of partially innervated (1.2%±1.2) or denervated (0.2%±0.6) NMJs identified. Gcn2$^{KO/KO}$; Gars$^{P278KY/+}$ mice have an increased percentage of fully innervated NMJs (66.8%±12.3) compared to Gcn2$^{+/+\ or\ +/KO}$; Gars$^{P278KY/+}$ (31.3%±19.9), and a decreased percentage of partially innervated (23.5%±9.7 vs 38.8%±11.3) and denervated (9.9%±8.3 vs 29.9%±17.2) NMJs. Analysis performed with 8-15 mice per grouped genotype. Values in FIGS. 6A, 6B, 6E, and 6K are mean±SD. Prior to grouping genotypes, all individual genotypes tested negatively for differences with one another. , p<0.01; *, p<0.001; ****=p<0.0001.

Gars$^{P278KY/+}$ mice typically contain a large percentage of partially innervated or denervated neuromuscular junctions (NMJs) in the gastrocnemius muscle. NMJs were scored as fully innervated if the axon terminal completely overlapped the post-synaptic muscle (FIG. 6G), partially innervated if some of the muscle was without axon coverage (FIG. 6H), and denervated if the axon was entirely absent from the muscle (FIG. 6I). Morphologically, Gcn2$^{+/+, +/KO or KO/KO}$; Gars$^{+/+}$ mice have NMJs with sharp staining in the classic "pretzel" shape. Fully innervated NMJs in Gcn$^{+/+ or +/KO}$; Gars$^{P278KY/+}$ mice tend to be fragmented and often do not display the pretzel morphology. In contrast, fully innervated NMJs in Gcn2$^{KO/KO}$; Gars$^{P278KY/+}$ mice largely retained the pretzel morphology (FIG. 6J). Moreover, Gcn2$^{KO/KO}$; Gars$^{P278KY/+}$ mice had a larger percentage of fully innervated NMJs (66.7%±12.3) and a smaller percentage of partially innervated (23.5%±9.7) and denervated (9.8%±8.2) NMJs compared to Gcn$^{+/+ or +/KO}$; Gars$^{P278KY/+}$ (31.3%±19.9 fully innervated, 38.8%±11.3 partially innervated, and 29.9%±17.2 denervated) (FIG. 6K). This return to Gcn2$^{+/+, +/KO or KO/KO}$; Gars$^{+/+}$ innervation status continues at least through 16 weeks of age (data not shown).

These data demonstrate that chronic activation of the ISR through GCN2 is detrimental to motor neurons. Partial rescue of CMT2D neuropathy is achieved by genetic removal of GCN2 as analyzed at 8 weeks of age. This rescue does not appear to be a delay in the development of neuropathy, as neuropathy is still alleviated at 16 weeks of age. Because removal of GCN2 and deactivation of the ISR provides long-term alleviation of CMT2D neuropathy in mice, GCN2 may be a promising drug target for future therapeutics in humans.

Example 6. The Integrated Stress Response is Activated in Alpha Motor Neurons of Mice with Dominant Mutations in Tyrosyl tRNA-Synthetase ($Yars^{E196K/E196K}$)

Figure 7A:
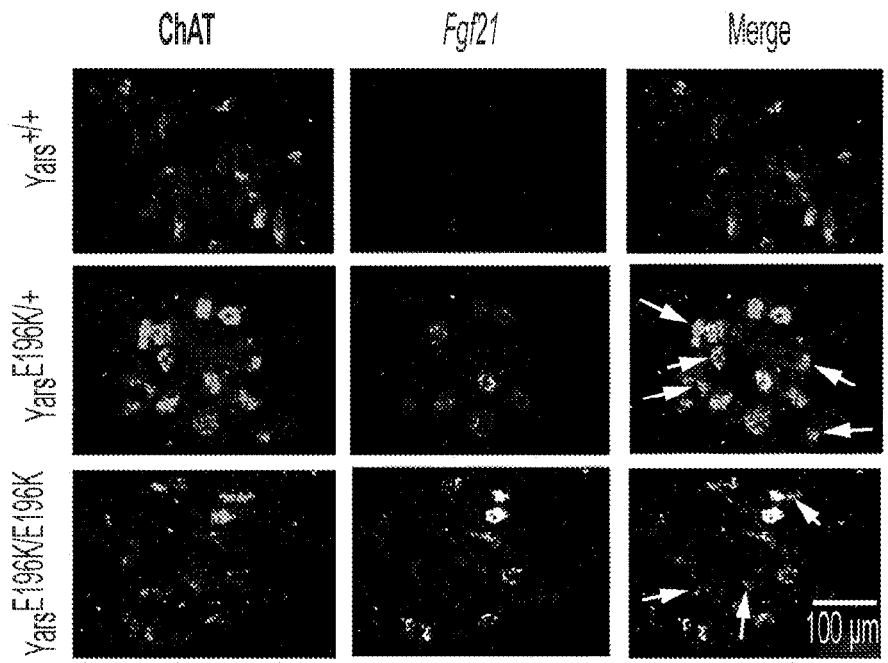
FIG. 7A shows that Yars$^{+/+}$ motor neurons of the spinal cord labeled with ChAT show now expression of the ATF4 target, Fgf21. A subset of Yars$^{E196K/+}$ motor neurons labeled with ChAT express Fgf21 at the pre-disease onset age of 7 months. A larger subset of Yars$^{E196K/E196K}$ motor neurons labeled with ChAT express Fgf21 at 7 months of age. Chat-labeled Yars$^{E196K/+}$ and Yars$^{E196K/E196K}$ motor neurons that do not express Fgf21 are marked with arrows.
Figure 7B:
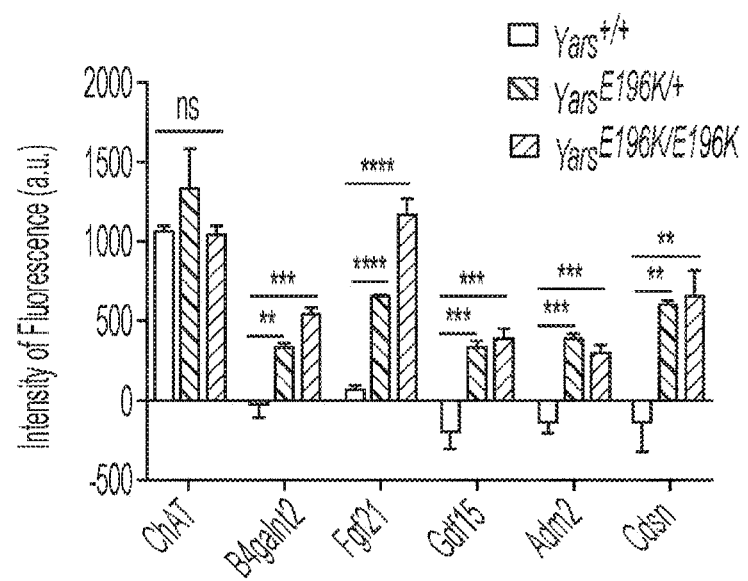
FIG. 7B shows the quantification of ATF4 target gene expression. Yars$^{E196K/+}$ and Yars$^{E196K/E196K}$ motor neurons express all 5 ATF4 target genes probed compared to little or no expression in Yars$^{+/+}$ motor neurons. B4galnt2 and Fgf21 show greater expression levels in Yars$^{E196K/E196K}$ motor neurons compared to Yars$^{E196K/+}$. Gdf15, Adm2, and Cdsn show approximately the same expression levels between Yars$^{E196K/E196K}$ and Yars$^{E196K/+}$.
Figure 7C:
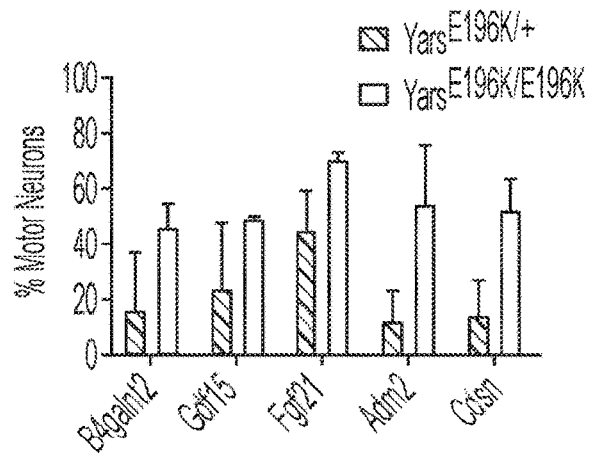
FIG. 7C shows that between 11-44% of Yars$^{E196K/+}$ motor neurons express any one of the 5 ATF4 target genes and between 46-67% of Yars$^{E196K/E196K}$ motor neurons express any one of the 5 ATF4 target genes.
Figure 7D:
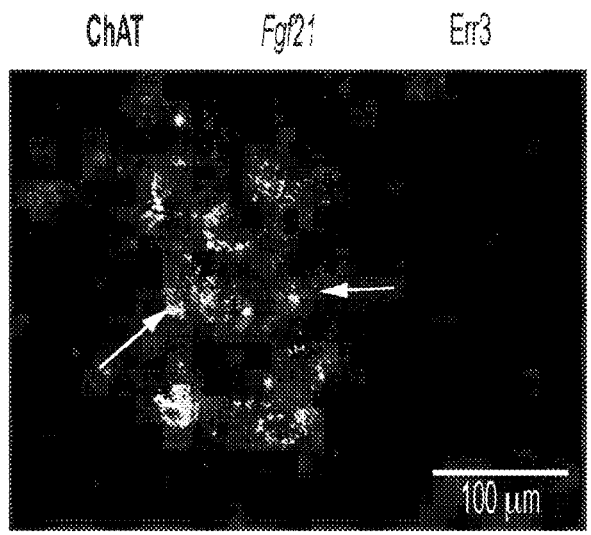
FIG. 7D shows that Yars$^{E196K/E196K}$ motor neurons that do not express Fgf21 are always labeled with the gamma motor neuron marker, Err3 (arrows).
Figure 7E:
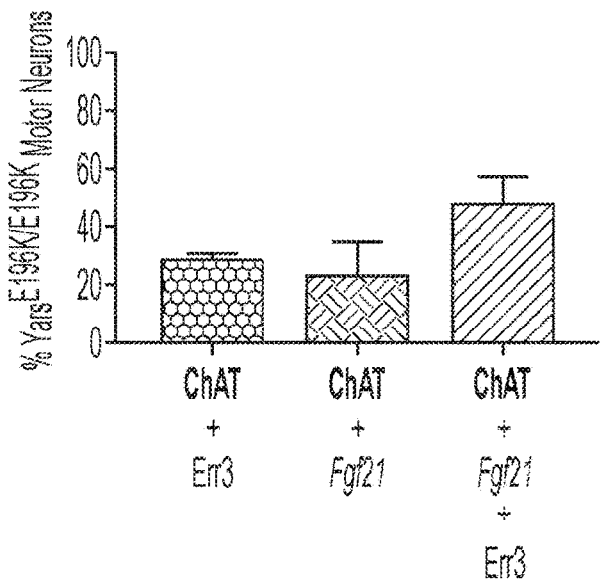
FIG. 7E shows the quantification of the experiment. Analysis was performed using 3 mice per genotype at 7 months of age. Values in FIG. 7B are the sum of average fluorescence per mouse per genotype±SD. Values in FIGS. 7C and 7E are mean±SD. , p<0.01, *, p<0.001; ****=p<0.0001.

We have recently characterized a mouse model of Dominant Intermediate CMT Type C (CMTDIC) with a human mutation in tryosyl tRNA-synthetase (YARS-E196K). By 7 months of age $YarS^{E196K/+}$ mice have no discernable neuropathy, but $Yars^{E196K/E196K}$ mice have reduced sciatic nerve conduction velocity and impaired performance on the wire hang test (data not shown) (manuscript in preparation). To test for possible similarities in gene expression signatures between mutant Yars and Gars motor neurons, we performed RNAscope in $YarS^{E196K/+}$ and $Yars^{E196K/E196K}$ spinal cords at 7 months of age, probing for the same five ATF4 target genes profiled in mutant Gars motor neurons. No expression of ATF4 target genes was seen in 7 month old $Yars^{+/+}$ mice (FIGS. 7A-7B). In contrast, all 5 genes were upregulated in 7 month old $YarS^{E196K/+}$ and $Yars^{E196K/E196K}$ motor neurons (FIGS. 7A-7B). Fgf21 and B4galnt2 showed higher expression in $Yars^{E196K/E196K}$ motor neurons compared to $YarS^{E196K/+}$ whereas Gdf15, Adm2, and Cdsn showed similar expression levels in both genotypes. As in Gars spinal cords, only a subset of motor neurons expressed ATF4 target genes (FIG. 7A). A higher subset of motor neurons showed ATF4 target gene expression in $Yars^{E196K/E196K}$ spinal cord compared to $YarS^{E196K/+}$ ranging from approximately 46-67% and 11-44%, respectively (FIG. 7C). In $Yars^{E196K/E196K}$ spinal cord, all motor neurons that were resistant to ATF4 target gene expression were positive for the gamma motor neuron marker, Err3, indicating that alpha motor neurons are the subtype of motor neuron expressing the disease signature in $Yars^{E196K/E196K}$ spinal cord, as in the $Gars^{P278KY/+}$ spinal cord (FIGS. 7D-7E). The presence of gene expression changes in $YarS^{E196K/+}$ motor neurons precedes overt neuropathy, which is also the case in the Gars mice. In addition, the percentage of motor neurons showing gene expression changes correlates with onset of overt neuropathy, as a greater subset of motor neurons in symptomatic $Yars^{E196K/E196K}$ mice express ATF4 target genes compared to asymptomatic $Yars^{E196K/+}$ mice at 7 months of age. The percentage of motor neurons showing gene expression changes also correlates with disease severity, as the very severe $GaES^{P278KY/+}$ mice show gene expression changes of all five ATF4 target genes in 70% of motor neurons, but the milder $Yars^{E196K/E196K}$ mice only show expression in 46-67% of motor neurons, depending on the gene. In the cases of B4galnt2 and Fgf21, the level of gene expression also correlates with onset of neuropathy, as higher expression is observed in $Yars^{E196K/E196K}$ mice compared to $YaES^{E196K/+}$ These correlations suggest that ATF4 target gene expression is strongly associated with the central disease mechanism. In addition, the striking similarities in mutant Gars and Yars gene expression signatures and in the patterns of cell type-specificity provide strong molecular and cellular evidence of a related disease mechanism in mouse models of two different ARS-associated forms of CMT.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. A method comprising administering to a subject an inhibitor of expression and/or activity of GCN2, wherein the subject has Charcot-Marie-Tooth (CMT) disease.

2. The method of claim 1, wherein the CMT disease is selected from CMT1, CMT2, CMT2D, diCMT, CMT2W, and CMT2N.

3. The method of claim 1, wherein the subject is a human.

4. The method of claim 1, wherein the inhibitor inhibits expression of GCN2.

5. The method of claim 1, wherein the inhibitor inhibits activity of GCN2.

6. The method of claim 1, wherein the inhibitor is a selected from polypeptides, polynucleotides, and small component drugs.

7. The method of claim 6, wherein the inhibitor is an antibody.

8. The method of claim 6, wherein the inhibitor is a programmable nuclease.

9. The method of claim 6, wherein the inhibitor is RNA interference component or an antisense RNA component.

10. The method of claim 6, wherein the inhibitor is a small component drug selected from the group consisting of A-92 (triazolo[4,5-d]pyrimidine derivative), indirubin-3-monoxime, SP600125, and a Syk inhibitor.

* * * * *